US008143252B2

(12) United States Patent
Figg et al.

(10) Patent No.: US 8,143,252 B2
(45) Date of Patent: Mar. 27, 2012

(54) TETRAHALOGENATED COMPOUNDS USEFUL AS INHIBITORS OF ANGIOGENESIS

(75) Inventors: William D. Figg, Fairfax, VA (US); Erin Gardner, Fairfax, VA (US); Michael Gutschow, Bonn (DE); Agnieszka Ambrozak, Buchs (CH)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 348 days.

(21) Appl. No.: 12/287,597

(22) Filed: Oct. 10, 2008

(65) Prior Publication Data

US 2009/0186913 A1    Jul. 23, 2009

Related U.S. Application Data

(63) Continuation-in-part of application No. PCT/US2007/008849, filed on Apr. 10, 2007.

(60) Provisional application No. 60/792,098, filed on Apr. 13, 2006.

(51) Int. Cl.
A01N 43/58 (2006.01)
A61K 31/50 (2006.01)

(52) U.S. Cl. .................. 514/247; 514/183; 544/224

(58) Field of Classification Search ............... 514/183
See application file for complete search history.

(56) References Cited

U.S. PATENT DOCUMENTS

| 3,560,495 | A | 2/1971 | Frankus et al. |
| 3,794,641 | A | 2/1974 | Görög et al. |
| 5,593,990 | A | 1/1997 | D'Amato |
| 6,080,742 | A | 6/2000 | Germann et al. |
| 6,110,941 | A | 8/2000 | Zimmer et al. |
| 6,458,810 | B1 | 10/2002 | Muller et al. |
| 6,500,845 | B1 | 12/2002 | Boehlke et al. |
| 7,084,160 | B2 | 8/2006 | Borzilleri et al. |
| 7,320,991 | B2 | 1/2008 | Figg et al. |
| 2003/0013739 | A1 | 1/2003 | Masferrer |
| 2003/0181428 | A1 | 9/2003 | Green et al. |
| 2005/0004087 | A1 | 1/2005 | D'Amato et al. |
| 2006/0211737 | A1 | 9/2006 | Huang et al. |
| 2007/0293519 | A1 | 12/2007 | Figg et al. |

FOREIGN PATENT DOCUMENTS

| GB | 1075420 | 7/1967 |
| WO | WO 97/37988 | 10/1997 |
| WO | WO 99/59960 | 11/1999 |
| WO | WO 02/068414 | 9/2002 |
| WO | WO 03/097052 | 11/2003 |
| WO | WO 2005/016326 | 2/2005 |

OTHER PUBLICATIONS

Osol et al., Remington's Pharmaceutical Sciences, 1980, Chapter 27: Structure-activity relationship and drug design, pp. 420-435.*
Dredge et al., "Novel thalidomide analogues display anti-angiogenic activity independently of immunomodulatory effects," *British Journal of Cancer* 87:1166-1172, 2002.
Dredge et al., "Immunological Effects of Thalidomides and Its Chemical and Functional Analogs," *Critical Reviews in Immunology* 22(5&6):425-437, 2002.
Dredge et al., "Recent developments in antiangiogenic therapy," *Expert Opin. Biol. Ther.* 2(8):953-966, 2002.
Dredge et al., "Thalidomide analogs as emerging anti-cancer drugs," *Anti-Cancer Drugs* 14:331-335, 2003.
Dredge et al., "Angiogenesis inhibitors in cancer therapy," *Current Opinion in Investigational Drugs* 4(5):667-674, 2003.
Hess et al., "Synthesis and Immunological Activity of Water-Soluble Thalidomide Prodrugs," *Bioorganic & Medicinal Chemistry* 9:1279-1291, 2001.
Gütschow et al., "Aza Analogues of Thalidomide: Synthesis and Evaluation as Inhibitors of Tumor Necrosis Factor-α Production In Vitro," *Bioorganic & Medicinal Chemistry* 9:1059-1065, 2001.
Hashimoto, "Novel Biological Response Modifiers Derived from Thalidomide," *Current Medicinal Chemistry* 5(3):163-178, 1998.
Hashimoto, "Structural Development of Biological Response Modifiers Based on Thalidomide," *Bioorganic & Medicinal Chemistry* 10:461-475, 2002.
Lepper et al., "Comparative Molecular Field Analysis and Comparative Molecular Similarity Indices Analysis of Thalidomide Analogues as Angiogenesis Inhibitors," *Journal of Medicinal Chemistry* 47(9):2219-2227, 2004.
Miyachi et al., "Inducer-Specified Regulators of Tumor Necrosis Factor Alpha Production," *Chem. Pharm. Bull.* 44(10):1980-1982, 1996.
Miyachi et al., "Novel Biological Response Modifiers: Phthalimides with Tumor Necrosis Factor-α Production-Regulating Activity," *Journal of Medicinal Chemistry* 40(18):2858-2865, 1997.
Ng et al., "Antiangiogenic Activity of N-substituted and Tetrafluorinated Thalidomide Analogues," *Cancer Research* 63:3189-3194, 2003.
Ng et al., "Antitumor Effects of Thalidomide Analogs in Human Prostate Cancer Xenografts Implanted in Immunodeficient Mice," *Clinical Cancer Research* 10:4192-4197,2004.
Shimazawa et al., "Antiangiogenic Activity of Tumor Necrosis Factor-α Production Regulators Derived from Thalidomide," *Biol. Pharm. Bull.* 22(2):224-226, 1999.
Shimazawa et al., "Novel Small Molecule Nonpeptide Aminopeptidase N Inhibitors with a Cyclic Imide Skeleton," *J. Enzyme Inhibition* 14:259-275, 1999.
Teubert et al., "5'-Substituted Thalidomide Analogs as Modulators of TNF-α," *Arch. Pharm. Pharm. Med Chem.* 371:7-12, 1998.
Zhu et al., "Thiothalidomides: Novel Isosteric Analogues of Thalidomide with Enhanced TNFα Inhibitory Activity," *Journal of Medicinal Chemistry* 46(24):5222-5229, 2003.
International Search Report from International Application No. PCT/US2007/008849, dated Aug. 13, 2007.

* cited by examiner

*Primary Examiner* — Jeffrey S. Lundgren
*Assistant Examiner* — Meghan Finn
(74) *Attorney, Agent, or Firm* — Klarquist Sparkman, LLP

(57) ABSTRACT

Methods for inhibiting a neoplasm in a subject and methods of inhibiting undesired angiogenesis that include administering to a subject a therapeutically effective amount of at least one novel tetrahalogenated compound, or a pharmaceutically acceptable salt thereof.

31 Claims, 6 Drawing Sheets

TETRAHALOGENATED COMPOUNDS USEFUL AS INHIBITORS OF ANGIOGENESIS

REFERENCE TO RELATED APPLICATION

This application is a continuation-in-part of International Application No. PCT/US2007/008849, filed Apr. 10, 2007, which claims the benefit of priority to U.S. Provisional Application No. 60/792,098 filed on Apr. 13, 2006, both of which are incorporated herein by reference in their entireties.

FIELD

The present disclosure relates to novel anti-neoplasm and/or anti-angiogenesis compounds.

BACKGROUND

Angiogenesis is the formation of new blood vessels from pre-existing vessels. Angiogenesis is prominent in solid tumor formation and metastasis. A tumor requires formation of a network of blood vessels to sustain the nutrient and oxygen supply for continued growth. Some tumors in which angiogenesis is important include most solid tumors and benign tumors, such as acoustic neuroma, neurofibroma, trachoma, and pyogenic granulomas. Prevention of angiogenesis could halt the growth of these tumors and the resultant damage due to the presence of the tumor.

It has been shown that there is a direct correlation between tumor microvessel density and the incidence of metastasis. Tumor cells themselves can produce factors that stimulate the proliferation of endothelial cells and new capillary growth. Angiogenesis is important in two stages of tumor metastasis. The first stage where angiogenesis stimulation is important is in the vascularization of the tumor, which allows tumor cells to enter the blood stream and to circulate throughout the body. After the tumor cells have left the primary site, and have settled into the secondary, metastasis site, angiogenesis must occur before the new tumor can grow and expand. Therefore, prevention of angiogenesis could lead to the prevention of metastasis of tumors and possibly contain the neoplastic growth at the primary site. These observations have led to the investigation of anti-angiogenic agents as possible therapeutic options for various cancers.

SUMMARY

Disclosed herein are methods for inhibiting a neoplasm in a subject that include administering to a subject a therapeutically effective amount of at least one compound, or pharmaceutically acceptable salts thereof, examples of which are described in detail below.

Also disclosed herein are methods of inhibiting undesired angiogenesis that include administering to a subject a therapeutically effective amount of at least one compound, or pharmaceutically acceptable salts thereof, examples of which are described in detail below.

Further disclosed herein are compounds, or pharmaceutically acceptable salts thereof, having a structure represented by the following formula I:

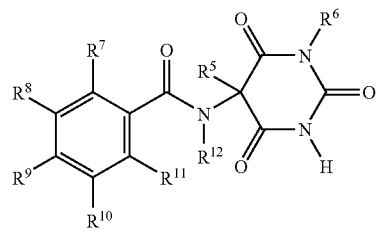

Formula I wherein (i) $R^5$ and $R^6$ are each independently H, alkyl, cycloalkyl, aryl, hydroxyl or alkenyl; $R^7$-$R^{11}$ are each F or Cl; and $R^{12}$ is H or alkyl; or (ii) $R^5$ and $R^6$ are each independently H, alkyl, cycloalkyl, aryl, hydroxyl or alkenyl; $R^7$-$R^{10}$ are each F or Cl; $R^{11}$ is H; and $R^{12}$ is H or alkyl; or (iii) $R^5$ and $R^6$ are each independently alkyl or cycloalkyl; $R^7$-$R^{10}$ are each F or Cl; and $R^{11}$ and $R^{12}$ together form a 5-member or 6-member ring structure. Examples of possible moieties for forming the ring structure of $R^{11}$ and $R^{12}$ include —C(O)-(isoindole-1,3-dione); —C(O)—NH— (2,3-dihydro-phthalazine-1,4-dione); —NH—C(O)-(1H-quinazoline-2,4-dione); —NH—C(S)-(2-thioxo-2,3-dihydro-1H-quinazolin-4-one); and —N=C($R^{13}$)— wherein $R^{13}$ is H, alkyl, aryl or alkylthio (3H-quinazolin-4-one).

According to one more specific embodiment of the class of compounds of formula I, there is disclosed herein tetrafluorinated compounds, or pharmaceutically acceptable salts thereof, having a structure represented by the following formula II:

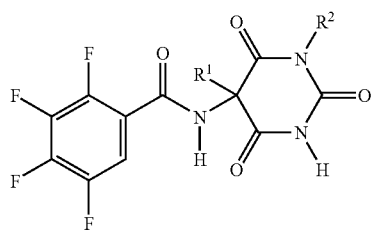

Formula II wherein $R^1$ is H, alkyl, or cycloalkyl; and $R^2$ is H, alkyl, cycloalkyl, aryl, hydroxyl, or alkenyl. In certain embodiments, $R^1$ is an alkyl selected from methyl, ethyl and propyl and $R^2$ is an alkyl selected from methyl, ethyl and propyl; a cyclohexyl; or a phenyl.

According to another more specific embodiment of formula I, disclosed herein are tetrafluorinated compounds, or pharmaceutically acceptable salts thereof, having a structure represented by the following formula III:

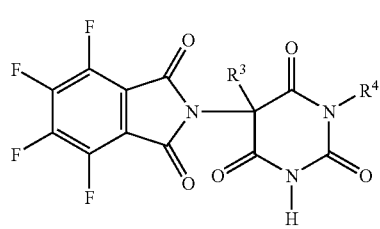

Formula III wherein $R^3$ is H, alkyl or cycloalkyl; and $R^4$ is H, alkyl, cycloalkyl, hydroxyl or alkenyl. In certain embodiments, $R^3$ is an alkyl selected from methyl, ethyl and propyl and $R^4$ is an alkyl selected from methyl, ethyl and propyl; or a cyclohexyl.

Pharmaceutical compositions that include the above-described compounds are also disclosed herein.

The foregoing and other objects, features, and advantages will become more apparent from the following detailed description, which proceeds with reference to the accompanying figures.

DETAILED DESCRIPTION

Figure 1:
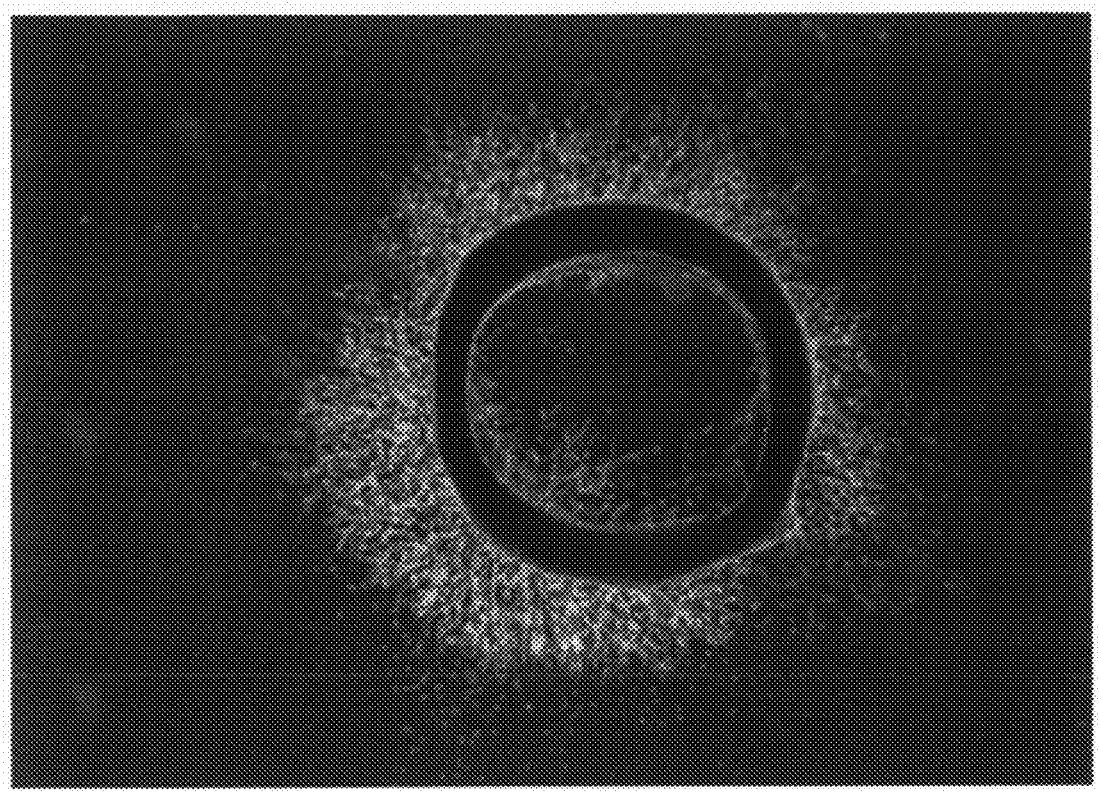
FIG. 1 is a photomicrograph of a control depicting a 1 mm section of a rat aorta ring after 4 days of incubation in a media containing 0.5% DMSO.
Figure 2:
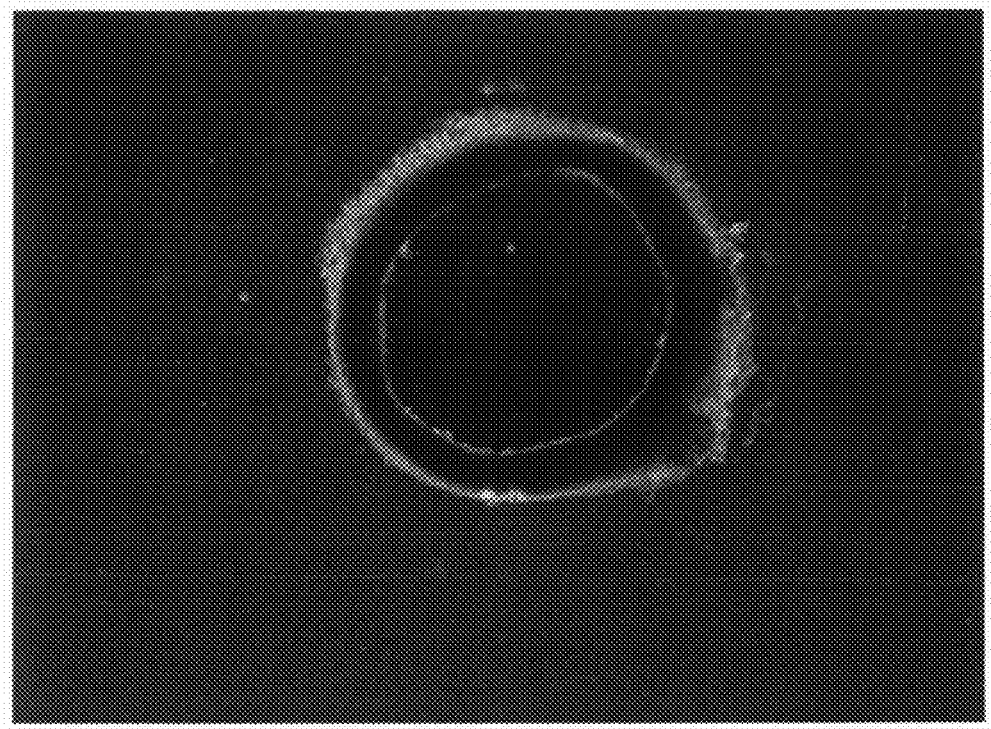
FIG. 2 is a photomicrograph depicting a 1 mm section of a rat aorta ring after 4 days of daily treatment with 50 µM of compound 20g.
Figure 3:
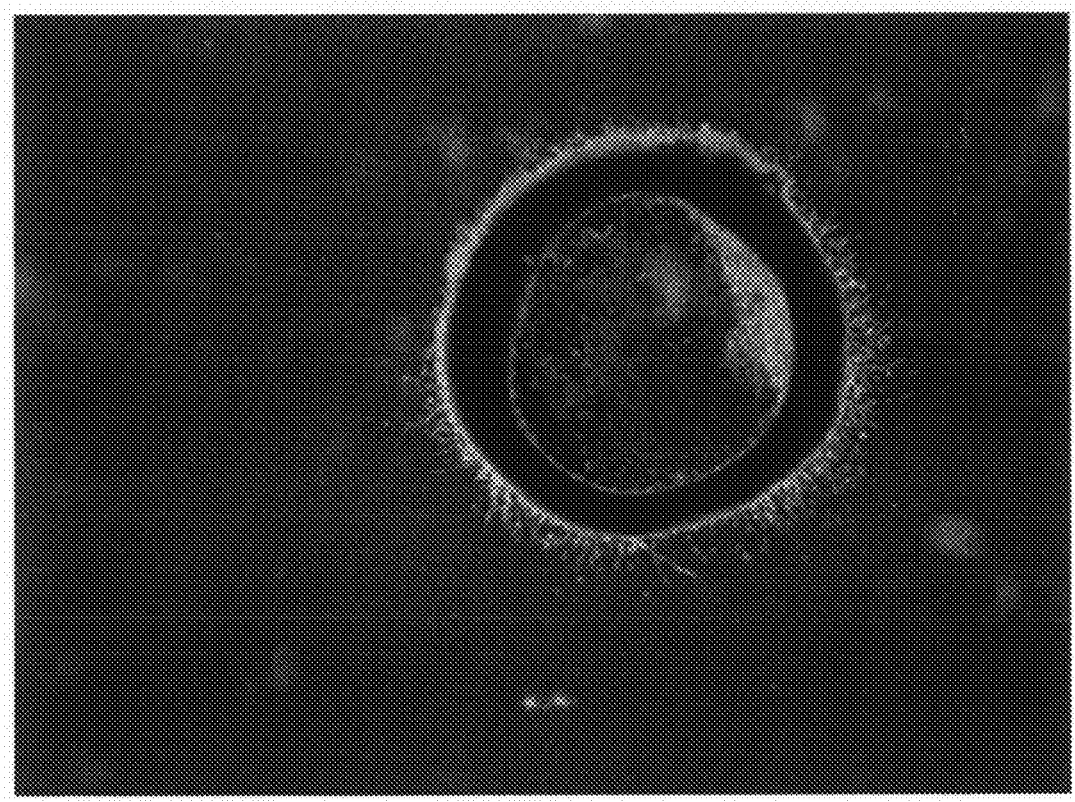
FIG. 3 is a photomicrograph depicting a 1 mm section of a rat aorta ring after 4 days of daily treatment with 50 µM of compound 20d.
Figure 4:
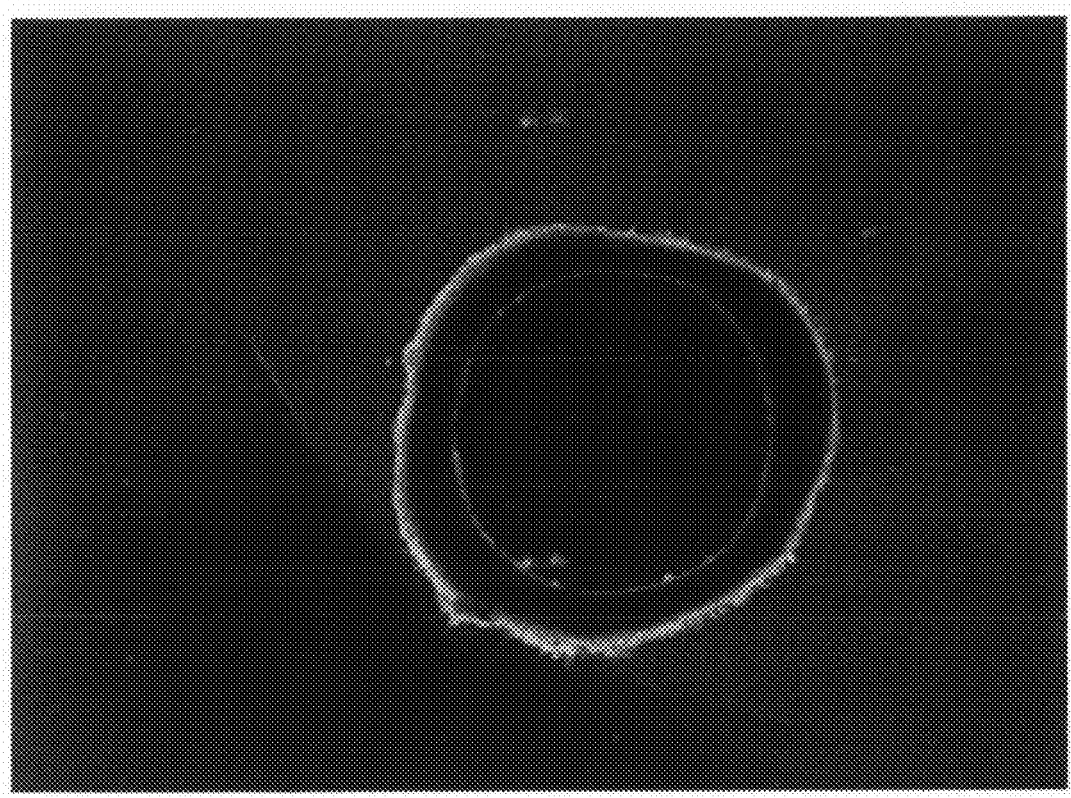
FIG. 4 is a photomicrograph depicting a 1 mm section of a rat aorta ring after 4 days of daily treatment with 50 µM of compound 19b.

For ease of understanding, the following terms used herein are described below in more detail:

"Acid" refers to a compound capable of transferring a hydrogen atom in solution. Acid is inclusive of, but not limited to, a carboxylic acid.

"Alkyl" refers to a branched or straight chain alkyl group containing only carbon and hydrogen. In certain embodiments, alkyl groups may contain one to twelve carbon atoms, particularly one to six carbon atoms. This term is further exemplified by groups such as methyl, ethyl, n-propyl, isobutyl, t-butyl, pentyl, pivalyl, heptyl, adamantyl, and cyclopentyl. Alkyl groups can either be unsubstituted or substituted with one or more substituents, e.g., halogen, alkoxy, cycloalkyl, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

"Amino acid moiety" refers to a moiety that contain one or more primary, secondary or tertiary amino groups and one or more acidic carboxyl groups (—COOH) or a moiety that is a derivative or residue of an amino acid in the sense that the moiety contains one or more amino groups (e.g., —NH$_2$) and one or more ester groups (i.e., —OC(O)—).

An "animal" is a living multicellular vertebrate organism, a category that includes, for example, mammals and birds.

"Antitumor" refers to antineoplastic activity, for example inhibiting the development or progression of a tumor, such as a malignant tumor, including local tumor growth or recurrence or metastatic spread.

"Aryl" refers to a monovalent unsaturated aromatic carbocyclic group having a single ring (e.g., phenyl) or multiple condensed rings (e.g., naphthyl or anthryl), which can optionally be unsubstituted or substituted with, e.g., halogen, alkyl, alkoxy, mercapto (—SH), alkylthio, trifluoromethyl, acyloxy, hydroxy, mercapto, carboxy, aryloxy, another aryl, arylalkyl, heteroaryl, amino, alkylamino, dialkylamino, morpholino, piperidino, pyrrolidin-1-yl, piperazin-1-yl, or other functionality.

"Angiogenesis" refers to the development of blood vessels. Accordingly, "anti-angiogenic activity" refers to the inhibition and/or complete cessation of angiogenesis.

"Cancer" or "malignant neoplasm" includes a neoplasm that has undergone characteristic anaplasia with loss of differentiation, increased rate of growth, invasion of surrounding tissue, and which is capable of metastasis.

"Cycloalkyl" includes a moiety that contains at least one cycloalkyl ring structure. There may be one or more ring structures including a bridged cyclic structure or a fused ring structure. The cycloalkyl may be unsubstituted or substituted with one or more substituents, e.g., halogen, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality. Illustrative cycloalkyl groups include cyclopropyl, cyclopentyl, cyclohexyl, cyclobutyl, and decahydronaphthyl.

"Halogen" refers to fluoro, bromo, chloro and iodo substituents.

A "mammal" includes both human and non-human mammals.

"Neoplasm" refers to an abnormal growth of cells or tissue, particularly a new growth of cells or tissue in which the growth is uncontrolled and progressive. A tumor is an example of a neoplasm.

"Pharmaceutically acceptable salts" of the presently disclosed compounds include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. "Pharmaceutically acceptable salts" are also inclusive of the free acid, base, and zwitterionic forms. Descriptions of suitable pharmaceutically acceptable salts can be found in *Handbook of pharmaceutical Salts, Properties, Selection and Use*, Wiley VCH (2002). Any chemical compound recited in this specification may also be administered as a pharmaceutically acceptable salt, free acid, anhydride or acid anhydride thereof.

A "pharmaceutical agent" or "drug" refers to a chemical compound or composition capable of inducing a desired therapeutic or prophylactic effect when properly administered to a subject.

"Subject" includes both human and animal subjects.

"Tumor" refers to a mass of cells resulting from excessive cellular multiplication. A tumor is a neoplasm that may be either malignant or non-malignant (benign) and includes both solid and non-solid tumors (such as hematologic malignancies). As used herein, this term also encompasses other cell types found in the tumor microenvironment, such as vascular endothelial cells, pericytes, fibroblasts and/or other stromal elements The above term descriptions are provided solely to aid the reader, and should not be construed to have a scope less than that understood by a person of ordinary skill in the art or as limiting the scope of the appended claims.

The singular terms "a," "an," and "the" include plural references unless context clearly indicates otherwise. It is further to be understood that all molecular weight or molecular mass values given for compounds are approximate, and are provided for description. Although methods and materials similar or equivalent to those described herein can be used in the practice or testing of this disclosure, suitable methods and materials are described below. In addition, the materials, methods, and examples are illustrative only and not intended to be limiting. All chemical compounds include both the (+) and (−) stereoisomers (as well as either the (+) or (−) stereoisomer), and any tautomers thereof.

Described herein are compounds that exhibit enhanced potency in the inhibition of undesirable angiogenesis, and methods for using these compounds to treat angiogenic-dependent diseases or neoplasms (e.g., solid tumors). In particular, the presently disclosed method provides for inhibiting unwanted angiogenesis in a human or animal by administering to the human or animal with the undesired angiogenesis a composition comprising an effective amount of the compounds. According to a more specific aspect, the method involves inhibiting angiogenesis by exposing a mass having the undesirable angiogenesis to an angiogenesis inhibiting amount of one or more compounds, or pharmaceutically acceptable salts of such compounds, wherein such compounds are selected from those of Formulae I, II and III as shown above. In a more particular embodiment, the compounds disclosed herein exhibit antitumor activity.

It should be recognized that although the compounds disclosed herein exhibit anti-angiogenic properties, the mechanism for action by the compounds upon neoplasms are not necessarily limited to anti-angiogenic mechanisms. For example, the compounds may also exhibit cytotoxic properties (that may be independent of any anti-angiogenic properties) that are useful for treating neoplasms.

Illustrative examples of compounds disclosed herein are shown below.

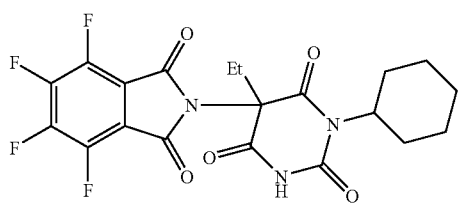

Compound 19i: 1-Cyclohexyl-5-ethyl-5-(4,5,6,7-tetrafluoro-1,3-dioxo-1,3-dihydro-isoindol-2-yl)-pyrimidine-2,4,6-trione

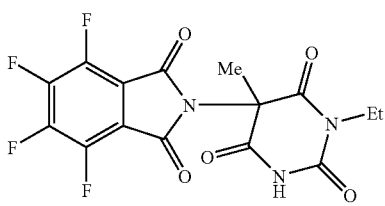

Compound 19f: 1-Ethyl-5-methyl-5-(4,5,6,7-tetrafluoro-1,3-dioxo-1,3-dihydro-isoindol-2-yl)-pyrimidine-2,4,6-trione

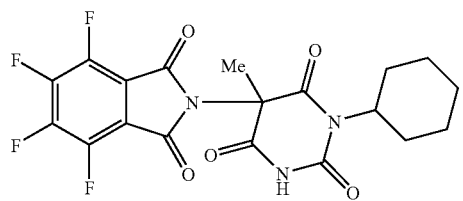

Compound 19h: 1-Cyclohexyl-5-methyl-5-(4,5,6,7-tetrafluoro-1,3-dioxo-1,3-dihydro-isoindol-2-yl)-pyrimidine-2,4,6-trione

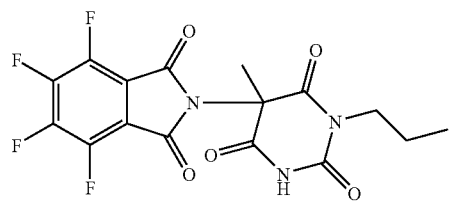

Compound 19b: 5-Methyl-1-propyl-5-(4,5,6,7-tetrafluoro-1,3-dioxo-1,3-dihydro-isoindol-2-yl)-pyrimidine-2,4,6-trione

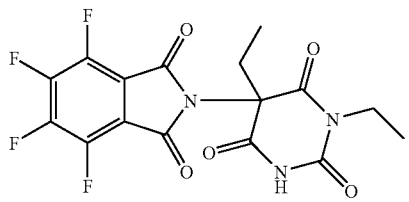

Compound 19d: 1,5-Diethyl-5-(4,5,6,7-tetrafluoro-1,3-dioxo-1,3-dihydro-isoindol-2-yl)-pyrimidine-2,4,6-trione

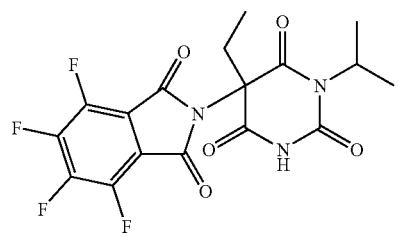

Compound 19g: 5-Ethyl-1-isopropyl-5-(4,5,6,7-tetrafluoro-1,3-dioxo-1,3-dihydro-isoindol-2-yl)-pyrimidine-2,4,6-trione

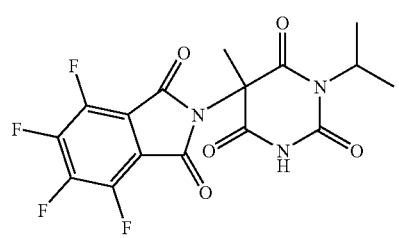

Compound 19c: 1-Isopropyl-5-methyl-5-(4,5,6,7-tetrafluoro-1,3-dioxo-1,3-dihydro-isoindol-2-yl)-pyrimidine-2,4,6-trione

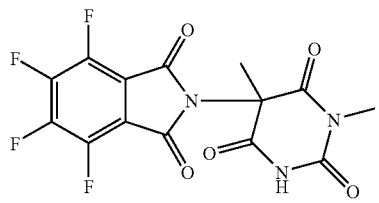

Compound 19a: 1,5-Dimethyl-5-(4,5,6,7-tetrafluoro-1,3-dioxo-1,3-dihydro-isoindol-2-yl)-pyrimidine-2,4,6-trione

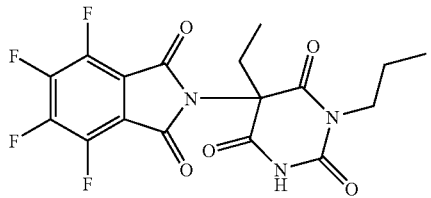

Compound 19e: 5-Ethyl-1-propyl-5-(4,5,6,7-tetrafluoro-1,3-dioxo-1,3-dihydro-isoindol-2-yl)-pyrimidine-2,4,6-trione

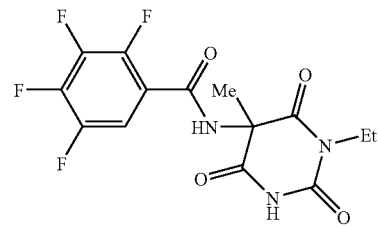

Compound 20f: —N-(1-Ethyl-5-methyl-2,4,6-trioxo-hexahydro-pyrimidin-5-yl)-2,3,4,5-tetrafluoro-benzamide

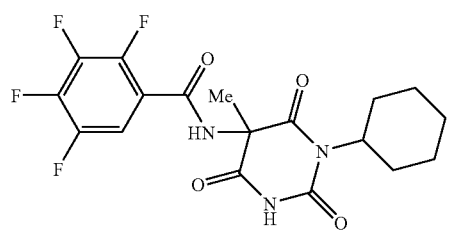

Compound 20h: N-(1-Cyclohexyl-5-methyl-2,4,6-trioxo-hexahydro-pyrimidin-5-yl)-2,3,4,5-tetrafluoro-benzamide

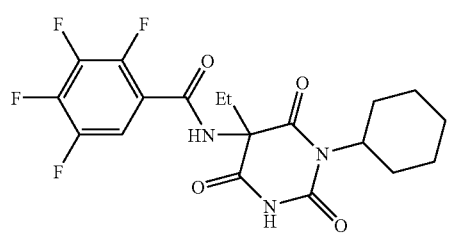

Compound 20i: —N-(1-Cyclohexyl-5-ethyl-2,4,6-trioxo-hexahydro-pyrimidin-5-yl)-2,3,4,5-tetrafluoro-benzamide

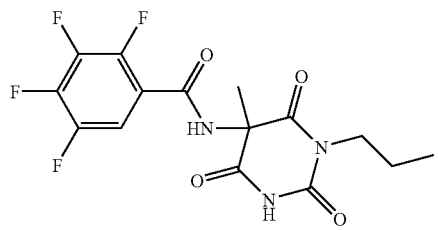

Compound 20b: 2,3,4,5-Tetrafluoro-N-(5-methyl-2,4,6-trioxo-1-propyl-hexahydro-pyrimidin-5-yl)-benzamide

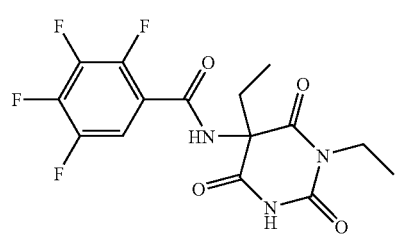

Compound 20d: N-(1,5-Diethyl-2,4,6-trioxo-hexahydro-pyrimidin-5-yl)-2,3,4,5-tetrafluoro-benzamide

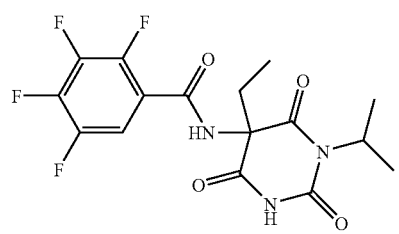

Compound 20g: N-(5-Ethyl-1-isopropyl-2,4,6-trioxo-hexahydro-pyrimidin-5-yl)-2,3,4,5-tetrafluoro-benzamide

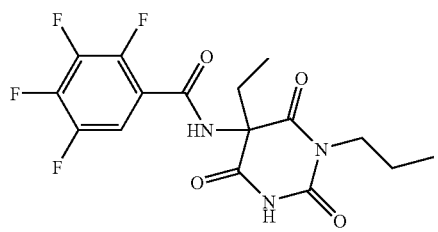

Compound 20e: N-(5-Ethyl-2,4,6-trioxo-1-propyl-hexahydro-pyrimidin-5-yl)-2,3,4,5-tetrafluoro-benzamide

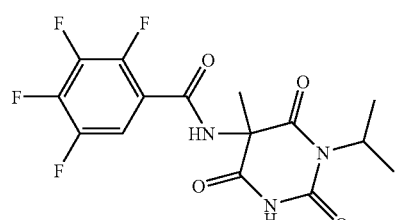

Compound 20c: 2,3,4,5-Tetrafluoro-N-(1-isopropyl-5-methyl-2,4,6-trioxo-hexahydro-pyrimidin-5-yl)-benzamide

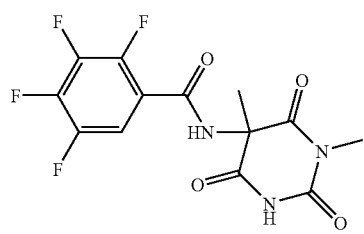

Compound 20a: N-(1,5-Dimethyl-2,4,6-trioxo-hexahydro-pyrimidin-5-yl)-2,3,4,5-tetrafluoro-benzamide

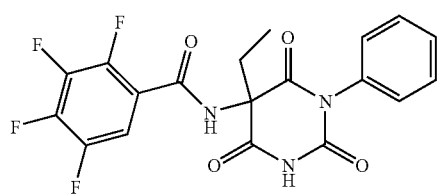

Compound 20k: N-(5-Ethyl-2,4,6-trioxo-1-phenyl-hexahydro-pyrimidin-5-yl)-2,3,4,5-tetrafluoro-benzamide These compounds may be synthesized by techniques known in the art. Examples of the synthesis of these compounds are described below in detail. All the compounds described below were synthesized as racemic mixtures.

General Synthesis Scheme for Tetrafluorophthalimidobarbituric Acids 19

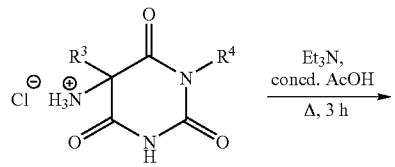

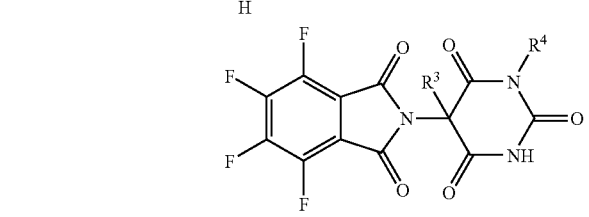

19a-e

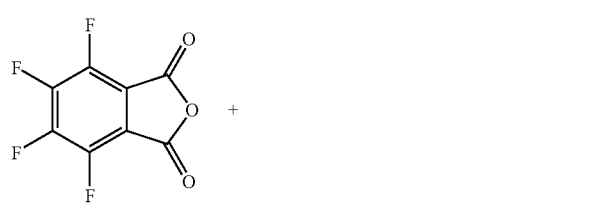

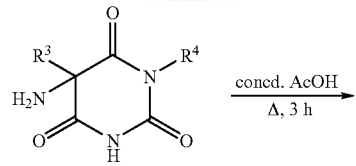

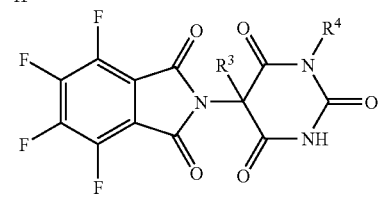

19f-i

General Synthesis Scheme for Tetrafluorobenzamide Derivatives 20

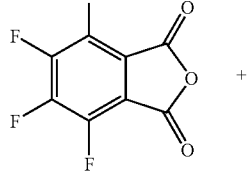

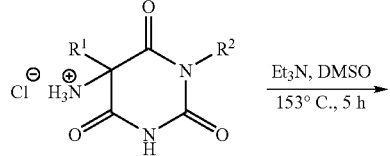

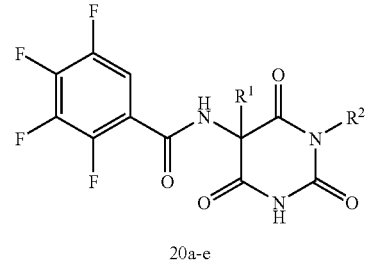

20a-e

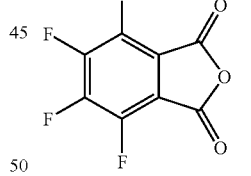

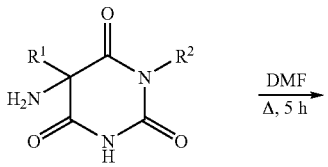

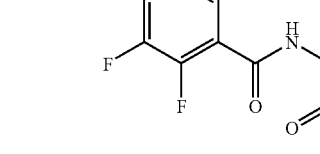

20g-k

1,5-Dimethyl-5-(4,5,6,7-tetrafluoro-1,3-dihydro-1,3-dioxo-2H-isoindol-2-yl)-2,4,6-(1H,3H,5H)-pyrimidinetrione (19a)

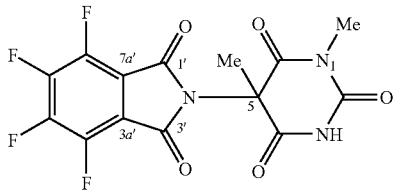

A mixture of 5-amino-1,5-dimethylbarbituric acid hydrochloride (0.31 g, 1.50 mmol), tetrafluorophthalic anhydride (0.40 g, 1.80 mmol) and Et$_3$N (0.21 mL, 0.15 g, 1.50 mmol) in glacial AcOH (11 mL) was stirred under reflux for 3 hours. The yellow solution was then allowed to cool down to room temperature and evaporated to dryness under reduced pressure. The oily residue was recrystallized from 70% EtOH to give 1,5-dimethyl-5-(tetrafluorophthalimido)-barbituric acid (19a) as white crystals.

| Yield (purified product): 0.22 g, (47%) | | | Melting point (purified product): 168-172° C. | | | | |
|---|---|---|---|---|---|---|---|
| Elemental analysis: | | | | | | | |
| C$_{14}$H$_7$F$_4$N$_3$O$_5$ | calcd.: | C | 45.05% | H | 1.89% | N | 11.26% |
| (373.22 g/mol) | found.: | C | 45.03% | H | 2.14% | N | 11.14% |

$^1$H NMR (DMSO-d$_6$) δ [ppm]:
2.17 (s, 3H, 5-CH$_3$), 3.17 (s, 3H, 1-CH$_3$), 12.21 (s, 1H, 3-H).

$^{13}$C NMR (DMSO-d$_6$) δ [ppm]:
21.13 (5-CH$_3$), 28.40 (1-CH$_3$), 63.70 (C-5), 112.48 (d, $^3$J (C, F)=7.5 Hz, C-3a', C-7a'), 143 (m, $^1$J (C, F)=266 Hz, C-4', C-7'), 145 (m, $^1$J (C, F)=264 Hz, C-5', C-6'), 149.32 (C-2), 162.61 (C-1', C-3'), 167.87, 168.61 (C-4, C-6).

MS (EI):
m/z (%): 373 (M$^+$, 94).

5-Methyl-1-propyl-5-(4,5,6,7-tetrafluoro-1,3-dihydro-1,3-dioxo-2H-isoindol-2-yl)-2,4,6(1H,3H,5H)-pyrimidinetrione (19b)

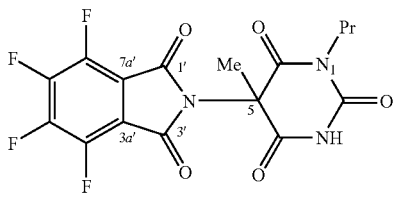

Compound 19b was synthesized in the same manner as described for 19a from 5-amino-5-methyl-1-propylbarbituric acid hydrochloride (0.38 g, 1.50 mmol). The crude product was recrystallized from EtOH (70%) to give 5-methyl-1-propyl-5-(tetrafluorophthalimido)-barbituric acid (19b) as white solid.

| Yield (purified product): 0.25 g, (42%) | | | Melting point (purified product): 173-177° C. | | | | |
|---|---|---|---|---|---|---|---|
| Elemental analysis: | | | | | | | |
| C$_{16}$H$_{11}$F$_4$N$_3$O$_5$ | calcd.: | C | 47.89% | H | 2.76% | N | 10.47% |
| (401.28 g/mol) | found.: | C | 47.59% | H | 2.87% | N | 10.23% |

$^1$H NMR (DMSO-d$_6$) δ [ppm]:
0.84 (t, J=7.4 Hz, 3H, 1-CH$_2$CH$_2$CH3), 1.51-1.58 (m, 2H, 1-CH$_2$CH$_2$CH$_3$), 2.16 (s, 3H, 5-CH$_3$), 3.66-3.78 (m, 2H, 1-CH$_2$CH$_2$CH$_3$), 12.19 (s, 1H, 3-H).

$^{13}$C NMR (DMSO-d$_6$) δ [ppm]:
10.97 (1-CH$_2$CH$_2$CH$_3$), 20.70 (1-CH$_2$CH$_2$CH$_3$), 21.20 (5-CH$_3$), 43.12 (1-CH$_2$CH$_2$CH$_3$), 63.82 (C-5), 112.47 (d, $^3$J (C, F)=7.5 Hz, C-3a', C-7a'), 143 (m, $^1$J (C, F)=267 Hz, C-4', C-7'), 145 (m, $^1$J (C, F)=263 Hz, C-5', C-6'), 149.10 (C-2), 162.62 (C-1', C-3'), 167.85, 168.58 (C-4, C-6).

MS (EI):
m/z (%): 401 (M$^+$, 18).

1-Isopropyl-5-methyl-5-(4,5,6,7-tetrafluoro-1,3-dihydro-1,3-dioxo-2H-isoindol-2-yl)-2,4,6(1H,3H,5H)-pyrimidinetrione (19c)

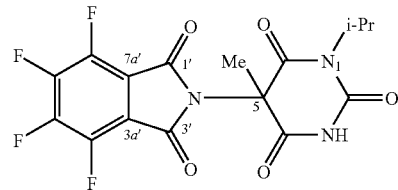

Compound 19c was synthesized in the same manner as described for 19a from 5-amino-1-isopropylbarbituric-5-methylbarbituric acid hydrochloride (0.35 g, 1.50 mmol). The crude product was recrystallized from EtOH (70%) to give 1-isopropyl-5-methyl-5-(tetrafluorophthalimido)barbituric acid (19c) as white solid.

| Yield (purified product): 0.25 g, (42%) | | | Melting point (purified product): 184-187° C. | | | | |
|---|---|---|---|---|---|---|---|
| Elemental analysis: | | | | | | | |
| C$_{16}$H$_{11}$F$_4$N$_3$O$_5$ | calcd.: | C | 47.89% | H | 2.76% | N | 10.47% |
| (401.28 g/mol) | found.: | C | 47.79% | H | 2.84% | N | 10.07% |

$^1$H NMR (DMSO-d$_6$) δ [ppm]:
1.34 (d, J=7.0 Hz, 3H, 1-CH(CH$_3$)$_2$), 1.35 (d, J=7.0 Hz, 3H, 1-CH(CH$_3$)$_2$), 2.15 (s, 3H, 5-CH$_3$), 4.82 (sept, J=7.0 Hz, 1H, 1-CH(CH$_3$)$_2$), 12.09 (s, 1H, 3-H).

$^{13}$C NMR (DMSO-d$_6$) δ [ppm]:
18.72, 19.74 1-CH(CH$_3$)$_2$), 21.02 (5-CH$_3$), 46.84 (1-CH(CH$_3$)$_2$), 64.21 (C-5), 112.53 (d, $^3$J (C, F)=7.4 Hz, C-3a', C-7a'), 143 (m, $^1$J (C, F)=266 Hz, C-4', C-7'), 145 (m, $^1$J (C, F)=264 Hz, C-5', C-6'), 148.95 (C-2), 162.65 (C-1', C-3') 167.66, 168.62 (C-4, C-6).

MS (EI):
m/z (%): 401 (M$^+$, 22).

1,5-Diethyl-5-(4,5,6,7-tetrafluoro-1,3-dihydro-1,3-dioxo-2H-isoindol-2-yl)-2,4,6-(1H,3H,5H)-pyrimidinetrione (19d)

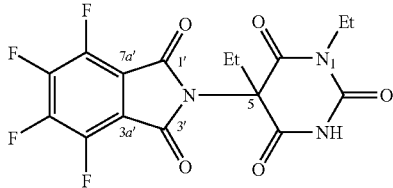

Compound 19d was synthesized in the same manner as described for 19a from 5-amino-1,5-diethylbarbituric acid hydrochloride (0.35 g, 1.50 mmol). The crude product was recrystallized from EtOH (70%) to give 1,5-diethyl-5-(tetrafluorophthalimido)barbituric acid (19d) as white crystals.

| Yield (purified product): 0.14 g, (23%) | Melting point (purified product): 152-154° C. | | | | | |
|---|---|---|---|---|---|---|
| Elemental analysis: | | | | | | |
| $C_{16}H_{11}F_4N_3O_5$ | calcd.: | C | 47.89% | H | 2.76% | N | 10.47% |
| (401.28 g/mol) | found.: | C | 47.98% | H | 2.74% | N | 10.24% |

$^1$H NMR (DMSO-$d_6$) δ [ppm]:
0.97 (t, J=7.4 Hz, 3H, 5-CH$_2$CH$_3$), 1.11 (t, J=7.1 Hz, 3H, 1-CH$_2$CH$_3$), 2.66 (q, J=7.4 Hz, 2H, 5-CH$_2$CH$_3$), 3.74-3.86 (m, 2H, 1-CH$_2$CH$_3$), 12.26 (s, 1H, 3-H).

$^{13}$C NMR (DMSO-$d_6$) δ [ppm]:
9.17 (5-CH$_2$CH$_3$), 12.88 (1-CH$_2$CH$_3$), 27.24 (5-CH$_2$CH$_3$), 36.87 (1-CH$_2$CH$_3$), 67.98 (C-5), 112.53 (d, $^3$J (C, F)=7.7 Hz, C-3a', C-7a'), 143 (m, $^1$J (C, F)=267 Hz, C-4', C-7'), 145 (m, $^1$J (C, F)=263 Hz, C-5', C-6'), 148.99 (C-2), 162.64 (C-1', C-3'), 166.89, 167.27 (C-4, C-6).

MS (EI):
m/z (%): 401 (M$^+$, 17).

5-Ethyl-1-propyl-5-(4,5,6,7-tetrafluoro-1,3-dihydro-1,3-dioxo-2H-isoindol-2-yl)-2,4,6(1H,3H,5H)-pyrimidinetrione (19e)

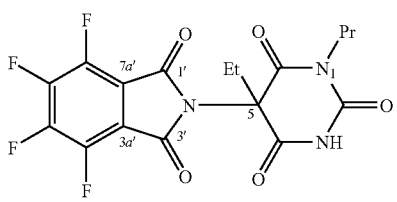

Compound 19e was synthesized in the same manner as described for 19a from 5-amino-5-ethyl-1-propylbarbituric acid hydrochloride (0.38 g, 1.50 mmol). The crude product was recrystallized from EtOH (70%) to give 5-ethyl-1-propyl-5-(tetrafluorophthalimido)-barbituric acid (19e) as white crystals.

| Yield (purified product): 0.29 g, (47%) | Melting point (purified product): 137-140° C. | | | | | |
|---|---|---|---|---|---|---|
| Elemental analysis: | | | | | | |
| $C_{17}H_{13}F_4N_3O_5$ | calcd.: | C | 49.17% | H | 3.16% | N | 10.12% |
| (415.30 g/mol) | found.: | C | 49.07% | H | 3.22% | N | 9.77% |

$^1$H NMR (DMSO-$d_6$) δ [ppm]:
0.85 (t, J=7.6 Hz, 3H, 1-CH$_2$CH$_2$CH$_3$), 0.97 (t, J=7.4 Hz, 3H 5-CH$_2$CH$_3$), 1.51-1.58 (m, 2H, 1-CH$_2$CH$_2$CH$_3$), 2.66 (q, J=7.4 Hz, 2H, 5-CH$_2$CH$_3$), 3.67-3.79 (m, 2H, 1-CH$_2$CH$_2$CH$_3$), 12.25 (s, 1H, 3-H).

$^{13}$C NMR (DMSO-$d_6$) δ [ppm]:
9.24 (5-CH$_2$CH$_3$), 11.02 (1-CH$_2$CH$_2$CH$_3$), 20.74 (1-CH$_2$CH$_2$CH$_3$), 27.28 (5-CH$_2$CH$_3$), 43.09 (1-CH$_2$CH$_2$CH$_3$), 68.06 (C-5), 112.52 (d, $^3$J (C, F)=6.0 Hz, C-3a', C-7a'), 143 (m, $^1$J (C, F)=267 Hz, C-4', C-7'), 145 (m, $^1$J (C, F)=263 Hz, C-5', C-6'), 149.25 (C-2), 162.63 (C-1', C-3'), 166.85, 167.56 (C-4, C-6).

MS (EI):
m/z (%): 415 (M$^+$, 30).

1-Ethyl-5-methyl-5-(4,5,6,7-tetrafluoro-1,3-dihydro-1,3-dioxo-2H-isoindol-2-yl)-2,4,6(1H,3H,5H)-pyrimidinetrione (19f)

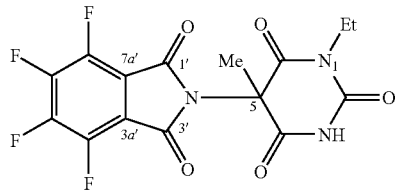

A mixture of 5-amino-1-ethyl-5-methylbarbituric acid (0.28 g, 1.50 mmol) and tetrafluorophthalic anhydride (0.40 g, 1.80 mmol) in glacial AcOH (111 mL) was stirred under reflux for 3 hours. The yellow solution was then allowed to cool down to room temperature and evaporated to dryness under reduced pressure. The oily residue was recrystallized from EtOH to give 1-ethyl-5-methyl-5-(tetrafluorophthalimido)barbituric acid (19f) as white crystals.

| Yield (purified product): 0.32 g, (55%) | Melting point (purified product): 178-184° C. | | | | | |
|---|---|---|---|---|---|---|
| Elemental analysis: | | | | | | |
| $C_{15}H_9F_4N_3O_5$ | calcd.: | C | 46.52% | H | 2.34% | N | 10.85% |
| (387.25 g/mol) | found.: | C | 46.27% | H | 2.35% | N | 10.53% |

$^1$H NMR (DMSO-$d_6$) δ [ppm]:
1.10 (t, J=7.1 Hz, 3H, 1-CH$_2$CH$_3$), 2.16 (s, 3H, 5-CH$_3$), 3.72-3.84 (m, 2H, 1-CH$_2$CH$_3$), 12.20 (s, 1H, 3-H).

$^{13}$C NMR (DMSO-$d_6$) δ [ppm]:
12.84 (1-CH$_2$CH$_3$), 21.11 (5-CH$_3$), 36.96 (1-CH$_2$CH$_3$), 63.78 (C-5), 112.53 (d, $^3$J (C, F)=7.9 Hz, C-3a', C-7a'), 143 (m, $^1$J (C, F)=257 Hz, C-4', C-7'), 145 (m, $^1$J (C, F)=253 Hz, C-5', C-6'), 148.88 (C-2), 162.66 (C-1', C-3'), 167.89, 168.28 (C-4, C-6).

MS (EI):
m/z (%): 387 (M$^+$, 100).

5-Ethyl-1-isopropyl-5-(4,5,6,7-tetrafluoro-1,3-dihydro-1,3-dioxo-2H-isoindol-2-yl)-2,4,6(1H,3H,5H)-pyrimidinetrione (19g)

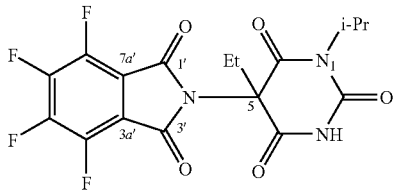

Compound 19g was prepared from 5-amino-5-ethyl-1-isopropylbarbituric acid (0.32 g, 1.50 mmol) using the same procedure described for 19f. The crude product was recrystallized from EtOH to give 5-ethyl-1-isopropyl-5-(tetrafluorophthalimido)barbituric acid (19g) as white crystals.

| Yield (purified product): | Melting point (purified product): |
|---|---|
| 0.35 g, (56%) | 134-139° C. |
| Elemental analysis: | |

| $C_{17}H_{13}F_4N_3O_5$ | calcd.: | C | 49.17% | H | 3.16% | N | 10.12% |
|---|---|---|---|---|---|---|---|
| (415.30 g/mol) | found.: | C | 49.08% | H | 3.16% | N | 9.66% |

$^1$H NMR (DMSO-$d_6$) δ [ppm]:
0.97 (t, J=7.5 Hz, 3H, 5-CH$_2$CH$_3$), 1.35 (d, J=6.9 Hz, 6H, 1-CH(CH$_3$)$_2$), 2.63-2.68 (m, 2H, 5-CH$_2$CH$_3$), 4.85 (sept, J=6.9 Hz, 1H, 1-CH(CH$_3$)$_2$), 12.16 (s, 1H, 3-H).

$^{13}$C NMR (DMSO-$d_6$) δ [ppm]:
9.20 (5-CH$_2$CH$_3$), 18.80, 19.78 (1-CH(CH$_3$)$_2$), 27.22 (5-CH$_2$CH$_3$), 46.90 (1-CH(CH$_3$)$_2$), 68.39 (C-5), 112.54 (d, $^3$J (C,F)=7.4 Hz, C-3a', C-7a'), 143 (m, $^1$J (C, F)=262 Hz, C-4', C-7'), 145 (m, $^1$J (C, F)=260 Hz, C-5', C-6'), 149.06 (C-2), 162.65 (C-1', C-3'), 166.67, 167.67 (C-4, C-6).

MS (EI):
m/z (%): 415 (M$^+$, 24).

1-Cyclohexyl-5-methyl-5-(4,5,6,7-tetrafluoro-1,3-dihydro-1,3-dioxo-2H-isoindol-2-yl)-2,4,6(1H,3H,5H)-pyrimidinetrione (19h)

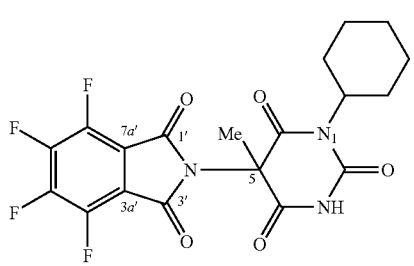

Compound 19h was prepared from 5-amino-1-cyclohexyl-5-methylbarbituric acid (0.36 g, 1.50 mmol) using the same procedure described for 19f. The crude product was recrystallized from EtOH to give 1-cyclohexyl-5-methyl-5-(tetrafluorophthalimido)barbituric acid (19h) as white crystals.

| Yield (purified product): | Melting point (purified product): |
|---|---|
| 0.31 g, (46%) | 208-211° C. |
| Elemental analysis: | |

| $C_{19}H_{15}F_4N_3O_5$ | calcd.: | C | 51.71% | H | 3.43% | N | 9.52% |
|---|---|---|---|---|---|---|---|
| (441.33 g/mol) | found.: | C | 51.35% | H | 3.44% | N | 9.45% |

$^1$H NMR (DMSO-$d_6$) δ [ppm]:
1.03-2.13 (m, 10H, CH$_2$-cyclohexyl), 2.14 (s, 3H, 5-CH$_3$), 4.41 (tt, J=12.2, 3.6 Hz, 1H, CH-cyclohexyl), 12.11 (s, 1H, 3-H).

$^{13}$C NMR (DMSO-$d_6$) δ [ppm]:
21.10 (5-CH$_3$), 25.02, 25.76, 25.87, 27.92, 29.17 (CH$_2$-cyclohexyl), 54.93 (CH-cyclohexyl), 64.27 (C-5), 112.48 (d, $^3$J (C, F)=8.2 Hz, C-3a', C-7a'), 143 (m, $^1$J (C, F)=261 Hz, C-4', C-7'), 145 (m, $^1$J (C, F)=261 Hz, C-5', C-6'), 149.05 (C-2), 162.63 (C-1', C-3'), 167.56, 168.78 (C-4, C-6).

MS (EI):
m/z (%): 441 (M$^+$, 2).

1-Cyclohexyl-5-ethyl-5-(4,5,6,7-tetrafluoro-1,3-dihydro-1,3-dioxo-2H-isoindol-2-yl)-2,4,6(1H,3H,5H)-pyrimidinetrione (19i)

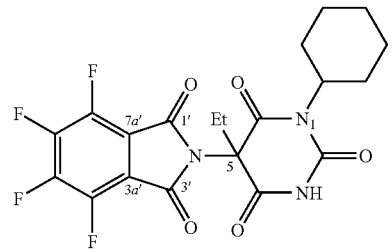

Compound 19i was prepared from 5-amino-1-cyclohexyl-5-ethylbarbituric acid (0.38 g, 1.50 mmol) using the same procedure described for 19f. The crude product was recrystallized from EtOH to give 1-cyclohexyl-5-ethyl-5-(tetrafluorophthalimido)barbituric acid (19i) as white crystals.

| Yield (purified product): | Melting point (purified product): |
|---|---|
| 0.50 g, (73%) | 172-176° C. |
| Elemental analysis: | |

| $C_{20}H_{17}F_4N_3O_5$ | calcd.: | C | 52.75% | H | 3.76% | N | 9.23% |
|---|---|---|---|---|---|---|---|
| (455.36 g/mol) | found.: | C | 52.71% | H | 3.96% | N | 8.96% |

$^1$H NMR (DMSO-$d_6$) δ [ppm]:
0.97 (t, J=7.4 Hz, 3H, 5-CH$_2$CH$_3$), 1.03-2.16 (m, 10H, CH$_2$-cyclohexyl), 2.64 (q, J=7.4 Hz, 2H, 5-CH$_2$CH$_3$), 4.44 (tt, J=12.2, 3.7 Hz, 1H, CH-cyclohexyl), 12.17 (s, 1H, 3-H).

$^{13}$C NMR (DMSO-$d_6$) δ [ppm]:
9.20 (5-CH$_2$CH$_3$), 24.99, 25.77, 25.86, 27.28, 28.04 (CH$_2$-cyclohexyl), 29.21 (5-CH$_2$CH$_3$), 54.99 (CH-cyclohexyl), 68.47 (C-5), 112.49-112.58 (m, C-3a', C-7a'), 143 (m, $^1$J (C, F)=268 Hz, C-4', C-7'), 145 (m, $^1$J (C, F)=258 Hz, C-5', C-6'), 149.19 (C-2), 162.64 (C—1', C-3'), 166.63, 167.78 (C-4, C-6).

MS (EI):
m/z (%): 455 (M$^+$, 3).

N-(Hexahydro-1,5-dimethyl-2,4,6-trioxo-5-pyrimidinyl)-2,3,4,5-tetrafluorobenzamide (20a)

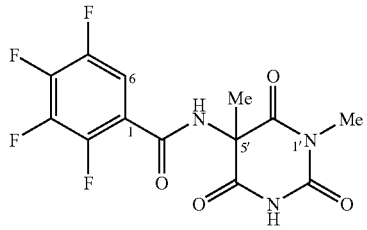

A mixture of 5-amino-1,5-dimethylbarbituric acid hydrochloride (0.42 g, 2 mmol), tetrafluorophthalic anhydride (0.44 g, 2 mmol), Et$_3$N (0.28 mL, 0.20 g, 2 mmol) and DMSO (3 mL) was stirred and heated at 153° C. for 5 hours. The reaction mixture was then allowed to cool down to room temperature and poured into water (10 mL). The oil that immediately formed was carefully removed from the solution, from which a solid precipitated after 4 days standing at room temperature. The precipitate was collected by filtration, washed with water and dried under reduced pressure to give 20a as yellow crystals.

| Yield (crude product): | Melting point (crude product): |  |  |  |  |
|---|---|---|---|---|---|
| 0.21 g, (29%) | 219-222° C. |  |  |  |  |
| Elemental analysis: | | | | | |
| C$_{13}$H$_9$F$_4$N$_3$O$_4$ × H$_2$O | calcd.: | C  42.75% | H  3.04% | N  11.51% | |
| (365.24 g/mol) | found.: | C  43.14% | H  2.87% | N  11.12% | |

$^1$H NMR (DMSO-d$_6$) δ [ppm]:
1.64 (s, 5'-CH$_3$), 3.13 (s, 3H, 1'-CH$_3$), 7.55-7.60 (m, 1H, 6-H), 9.77 (s, 1H, N—H), 11.73 (s, 1H, 3'-H).
$^{13}$C NMR (DMSO-d$_6$) δ [ppm]:
22.69 (5'-CH$_3$), 28.03 (1'-CH$_3$), 59.72 (C-5'), 111.96 (d, $^2$J (C, F)=20.3 Hz, C-6), 118.08-118.25 (m, C-1), 140 (m, $^1$J (C, F)=250 Hz, C-3), 142 (m, $^1$J (C, F)=254 Hz, C-4), 145 (m, $^1$J (C, F)=250 Hz, C-5), 146 (m, $^1$J (C, F)=245 Hz, C-2), 150.06 (C-2'), 161.71 (C=O), 169.59, 170.46 (C-4', C-6').
MS (EI): m/z (%): 347 (M$^+$, 54).

N-(Hexahydro-5-methyl-2,4,6-trioxo-1-propyl-5-pyrimidinyl)-2,3,4,5-tetrafluorobenzamide (20b)

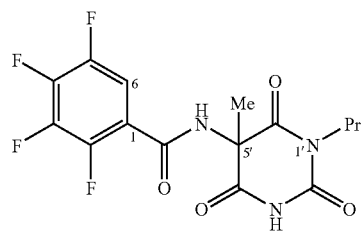

The method for the preparation of 20b was the same as for 20a, but using 5-amino-5-methyl-1-propylbarbituric acid hydrochloride (0.51 g, 2 mmol). 5-Methyl-1-propyl-5-(tetrafluorobenzamido)barbituric acid (20b) was obtained as yellow crystals and did not require further purification.

| Yield (crude product): | Melting point (crude product): |  |  |  |  |
|---|---|---|---|---|---|
| 0.14 g, (17%) | 83-87° C. |  |  |  |  |
| Elemental analysis: | | | | | |
| C$_{15}$H$_{13}$F$_4$N$_3$O$_4$ × H$_2$O | calcd.: | C  44.78% | H  4.01% | N  10.45% | |
| (402.30 g/mol) | found.: | C  45.15% | H  3.82% | N  10.16% | |

$^1$H NMR (DMSO-d$_6$) δ [ppm]:
0.84 (t, J=7.4 Hz, 3H, 1'-CH$_2$CH$_2$CH$_3$), 1.49-1.56 (m, 2H, 1'-CH$_2$CH$_2$CH$_3$), 1.64 (s, 3H, 5'-CH$_3$), 3.64-3.76 (m, 2H, 1'-CH$_2$CH$_2$CH$_3$), 7.53-7.58 (m, 1H, 6-H), 9.76 (s, 1H, N—H), 11.70 (s, 1H, 3'-H).
$^{13}$C NMR (DMSO-d$_6$) δ [ppm]:
11.03 (1'-CH$_2$CH$_2$CH$_3$), 20.80 (1'-CH$_2$CH$_2$CH$_3$), 22.73 (5'-CH$_3$), 42.58 (1'-CH$_2$CH$_2$CH$_3$), 59.81 (C-5'), 111.92 (d, $^2$J (C, F)=20.6 Hz, C-6), 118.10-118.27 (m, C-1), 140 (m, $^1$J (C, F)=250 Hz, C-3), 142 (m, $^1$J (C, F)=254 Hz, C-4), 145 (m, $^1$J (C, F)=250 Hz, C-5), 146 (m, $^1$J (C, F)=245 Hz, C-2), 149.84 (C-2'), 161.68 (C=O), 169.59, 170.30 (C-4', C-6').
MS (EI):
m/z (%): 375 (M$^+$, 34).

N-(Hexahydro-1-isopropyl-5-methyl-2,4,6-trioxo-5-pyrimidinyl)-2,3,4,5-tetrafluorobenzamide (20c)

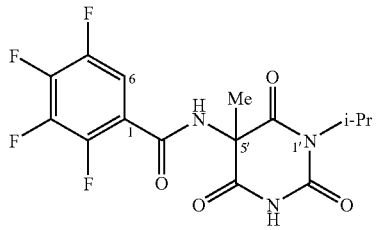

The method for the preparation of 20c was the same as for 20a, but using 5-amino-1-isopropyl-5-methylbarbituric acid hydrochloride (0.47 g, 2 mmol). 1-Isopropyl-5-methyl-5-(tetrafluorobenzamido)barbituric acid (20c) was obtained as yellow crystals and did not require further purification.

| Yield (crude product): | Melting point (crude product): |  |  |  |  |
|---|---|---|---|---|---|
| 70 mg, (9%) | 225-229° C. |  |  |  |  |
| Elemental analysis: | | | | | |
| C$_{15}$H$_{13}$F$_4$N$_3$O$_4$ | calcd.: | C  48.01% | H  3.49% | N  11.20% | |
| (375.28 g/mol) | found.: | C  47.41% | H  3.55% | N  10.60% | |

$^1$H NMR (DMSO-d$_6$) δ [ppm]:
1.33 (d, J=6.3 Hz, 3H, 1'-CH(CH$_3$)$_2$), 1.34 (d, J=6.3 Hz, 3H, 1'-CH(CH$_3$)$_2$), 1.62 (s, 3H, 5'-CH$_3$), 4.83 (sept, J=6.3 Hz, 1H, 1'-CH(CH$_3$)$_2$), 7.54-7.59 (m, 1H, 6-H), 9.70 (s, 1H, N—H), 11.59 (s, 1H, 3'-H).
$^{13}$C NMR (DMSO-d$_6$) δ [ppm]:
19.01, 19.80 (1'-CH(CH$_3$)$_2$), 22.59 (5'-CH$_3$), 46.04 (1'-CH(CH$_3$)$_2$), 60.16 (C-5'), 111.95 (d, $^2$J (C, F)=20.3 Hz, C-6), 118.17-118.33 (m, C-1), 140 (m, $^1$J (C, F)=251 Hz, C-3), 142 (m, $^1$J (C, F)=253 Hz, C-4), 145 (m, $^1$J (C, F)=246 Hz, C-5), 146 (m, $^1$J (C, F)=245 Hz, C-2), 149.67 (C-2'), 161.61 (C=O), 169.43, 170.28 (C-4', C-6').
MS (EI):
m/z (%): 375 (M$^+$, 56).

N-(1,5-Diethyl-hexahydro-2,4,6-trioxo-5-pyrimidinyl)-2,3,4,5-tetrafluorobenzamide (20d)

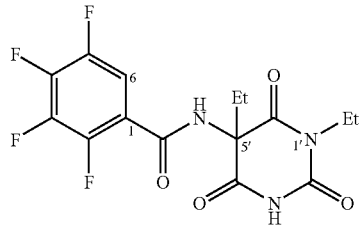

The method for the preparation of 20d was the same as for 20a, but using 5-amino-1,5-diethylbarbituric acid hydrochloride (0.47 g, 2 mmol). Pure 1,5-diethyl-5-(tetrafluoro-benzamido)barbituric acid (20d) was obtained as yellow crystals.

| Yield (crude product): | Melting point (crude product): |
|---|---|
| 0.14 g, (18%) | 163-167° C. |

| Elemental analysis: | | | | | | |
|---|---|---|---|---|---|---|
| $C_{15}H_{13}F_4N_3O_4$ | calcd.: | C | 48.01% | H | 3.49% | N | 11.20% |
| (375.28 g/mol) | found.: | C | 47.76% | H | 3.54% | N | 10.66% |

$^1$H NMR (DMSO-$d_6$) δ [ppm]:
0.89 (t, J=7.6 Hz, 3H, 5'-CH$_2$CH$_3$), 1.09 (t, J=7.1 Hz, 3H, 1'-CH$_2$CH$_3$), 2.01-2.06 (m, 2H, 5'-CH$_2$CH$_3$), 3.73-3.84 (m, 2H, 1'-CH$_2$CH$_3$), 7.53-7.58 (m, 1H, 6-H), 9.65 (s, 1H, N—H), 11.80 (s, 1H, 3'-H).

$^{13}$C NMR (DMSO-$d_6$) δ [ppm]:
7.71 (5'-CH$_2$CH$_3$), 13.01 (1'-CH$_2$CH$_3$), 29.90 (5'-CH$_2$CH$_3$), 36.30 (1'-CH$_2$CH$_3$), 63.70 (C-5'), 112.00 (d, 2J (C, F)=20.1 Hz, C-6), 118.24-118.42 (m, C-1), 140 (m, $^1$J (C, F)=251 Hz, C-3), 142 (m, $^1$J (C, F)=254 Hz, C-4), 145 (m, $^1$J (C, F)=251 Hz, C-5), 146 (m, $^1$J (C, F)=245 Hz, C-2), 149.70 (C-2'), 161.88 (C=O), 168.82, 169.20 (C-4', C-6').

MS (EI):
m/z (%): 375 (M$^+$, 15).

N-(5-Ethyl-hexahydro-2,4,6-trioxo-1-propyl-5-pyrimidinyl)-2,3,4,5-tetrafluorobenzamide (20e)

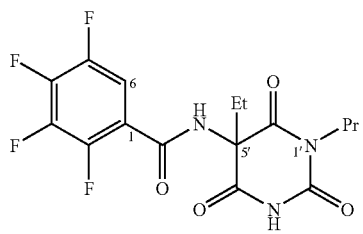

The method for the preparation of 20e was the same as for 20a, but using 5-amino-5-ethyl-1-propylbarbituric acid hydrochloride (0.51 g, 2 mmol). Pure 5-ethyl-1-propyl-5-(tetra-fluorobenzamido)barbituric acid (20e) was obtained as white crystals.

| Yield (crude product): | Melting point (crude product): |
|---|---|
| 0.10 g, (12%) | 79-82° C. |

| Elemental analysis: | | | | | | |
|---|---|---|---|---|---|---|
| $C_{16}H_{15}F_4N_3O_4$ × H$_2$O | calcd.: | C | 47.18% | H | 4.21% | N | 10.32% |
| (407.32 g/mol) | found.: | C | 46.62% | H | 4.16% | N | 10.00% |

$^1$H NMR (DMSO-$d_6$) δ [ppm]:
0.85 (t, J=7.4 Hz, 3H, 1'-CH$_2$CH$_2$CH$_3$), 0.90 (t, J=7.6 Hz, 3H, 5'-CH$_2$CH$_3$), 1.49-1.56 (m, 2H, 1'-CH$_2$CH$_2$CH$_3$), 2.01-2.05 (m, 2H, 5'-CH$_2$CH$_3$), 3.66-3.77 (m, 2H, 1'-CH$_2$CH$_2$CH$_3$), 7.52-7.57 (m, 1H, 6-H), 9.65 (s, 1H, N—H), 11.79 (s, 1H, 3'-H).

$^{13}$C NMR (DMSO-$d_6$) δ [ppm]:
8.47 (5'-CH$_2$CH$_3$), 11.83 (1'-CH$_2$CH$_2$CH$_3$), 21.60 (1'-CH$_2$CH$_2$CH$_3$), 30.63 (5'-CH$_2$CH$_3$), 43.33 (1'-CH$_2$CH$_2$CH$_3$), 64.49 (C-5'), 112.70 (d, $^2$J (C, F)=20.1 Hz, C-6), 119.00-119.09 (m, C-1), 141 (m, $^1$J (C, F)=249 Hz, C-3), 142 (m, $^1$J (C, F)=252 Hz, C-4), 146 (m, $^1$J (C, F)=251 Hz, C-5), 147 (m, $^1$J (C, F)=240 Hz, C-2), 150.69 (C-2'), 162.62 (C=O), 169.54, 170.21 (C-4', C-6').

MS (EI):
m/z (%): 389 (M$^+$, 20).

N-(1-Ethyl-hexahydro-5-methyl-2,4,6-trioxo-5-pyrimidinyl)-2,3,4,5-tetrafluorobenzamide (20f)

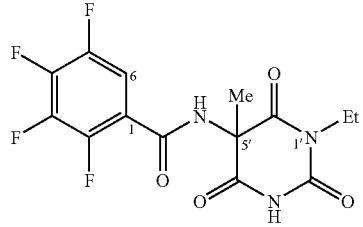

A mixture of 5-amino-1-ethyl-5-methylbarbituric acid (0.37 g, 2 mmol), tetrafluorophthalic anhydride (0.44 g, 2 mmol) and DMF (14 mL) was stirred under reflux for 5 hours. The yellow solution was then allowed to cool down to room temperature and poured into water (50 mL). The precipitate that formed was collected by filtration and dried under reduced pressure to give 20f as white crystals.

| Yield (crude product): | Melting point (crude product): |
|---|---|
| 0.63 g, (87%) | 207-212° C. |

| Elemental analysis: | | | | | | |
|---|---|---|---|---|---|---|
| $C_{14}H_{11}F_4N_3O_4$ | calcd.: | C | 46.55% | H | 3.07% | N | 11.63% |
| (361.25 g/mol) | found.: | C | 46.93% | H | 3.30% | N | 12.05% |

$^1$H NMR (DMSO-$d_6$) δ [ppm]:
1.08 (t, J=7.1 Hz, 3H, 1'-CH$_2$CH$_3$), 1.63 (s, 3H, 5'-CH$_3$), 3.71-3.81 (m, 2H, 1'-CH$_2$CH$_3$), 7.54-7.60 (m, 1H, 6-H), 9.76 (s, 1H, N—H), 11.70 (s, 1H, 3'-H).

$^{13}$C NMR (DMSO-$d_6$) δ [ppm]:
12.96 (1'-CH$_2$CH$_3$), 22.62 (5'-CH$_3$), 36.34 (1'-CH$_2$CH$_3$), 59.77 (C-5'), 111.95 (d, $^2$J (C, F)=20.8 Hz, C-6), 118.08-118.25 (m, C-1), 140 (m, $^1$J (C, F)=253 Hz, C-3), 142 (m, $^1$J (C, F)=254 Hz, C-4), 145 (m, $^1$J (C, F)=250 Hz, C-5), 146 (m, $^1$J (C, F)=248 Hz, C-2), 149.61 (C-2'), 161.70 (C=O), 169.60, 169.97 (C-4', C-6').

MS (EI): m/z (%): 361 (M$^+$, 83).

N-(5-Ethyl-hexahydro-1-isopropyl-2,4,6-trioxo-5-pyrimidinyl)-2,3,4,5-tetrafluorobenzamide (20g)

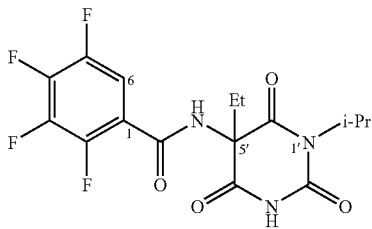

Compound 20g was prepared by the same method described for 20f using 5-amino-5-ethyl-1-isopropylbarbituric acid (0.37 g, 2 mmol). The crude 5-ethyl-1-isopropyl-5-(tetrafluoro-benzamido)barbituric acid (20g) was obtained as white crystals and did not require further purification.

| Yield (crude product): | | | Melting point (crude product): | | | |
|---|---|---|---|---|---|---|
| 0.71 g, (91%) | | | 166-171° C. | | | |
| Elemental analysis: | | | | | | |
| $C_{16}H_{15}F_4N_3O_4$ | calcd.: | C | 49.36% | H | 3.88% | N | 10.79% |
| (389.30 g/mol) | found.: | C | 49.74% | H | 4.02% | N | 10.78% |

$^1$H NMR (DMSO-d$_6$) δ [ppm]:
0.90 (t, J=7.4 Hz, 3H, 5'-CH$_2$CH$_3$), 1.34 (d, J=7.0 Hz, 6H, 1'-CH(CH$_3$)$_2$), 2.02 (q, J=7.4 Hz, 2H, 5'-CH$_2$CH$_3$), 4.86 (sept, J=7.0 Hz, 1H, 1'-CH(CH$_3$)$_2$), 7.52-7.57 (m, 1H, 6-H), 9.60 (s, 1H, N—H), 11.68 (s, 1H, 3'-H).

$^{13}$C NMR (DMSO-d$_6$) δ [ppm]:
7.74 (5'-CH$_2$CH$_3$), 19.08, 19.81 (1'-CH(CH$_3$)$_2$), 29.91 (5'-CH$_2$CH$_3$), 46.12 (1'-CH(CH$_3$)$_2$), 64.03 (C-5'), 111.99 (d, $^2$J (C, F)=20.6 Hz, C-6), 118.32-118.50 (m, C-1), 140 (m, $^1$J (C, F)=250 Hz, C-3), 142 (m, $^1$J (C, F)=253 Hz, C-4), 145 (m, $^1$J (C, F)=250 Hz, C-5), 146 (m, $^1$J (C, F)=246 Hz, C-2), 149.76 (C-2'), 161.81 (C=O), 168.69, 169.51 (C-4', C-6').

MS (EI):
m/z (%): 389 (M$^+$, 42).

N-(1-Cyclohexyl-hexahydro-5-methyl-2,4,6-trioxo-5-pyrimidinyl)-2,3,4,5-tetrafluorobenzamide (20h)

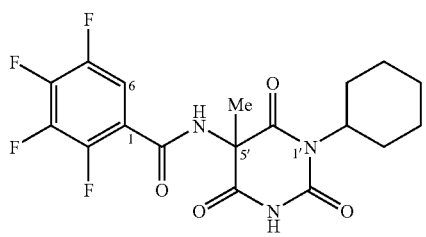

Compound 20h was prepared by the same method described for 20f using 5-amino-1-cyclohexyl-5-methylbarbituric acid (0.48 g, 2 mmol). The crude 1-cyclohexyl-5-methyl-5-(tetrafluorobenzamido)barbituric acid (20h) was obtained as yellow crystals and did not require further purification.

| Yield (crude product): | | | Melting point (crude product): | | | |
|---|---|---|---|---|---|---|
| 0.76 g, (92%) | | | 232-234° C. | | | |
| Elemental analysis: | | | | | | |
| $C_{18}H_{17}F_4N_3O_4$ | calcd.: | C | 52.05% | H | 4.13% | N | 10.12% |
| (415.34 g/mol) | found.: | C | 52.10% | H | 4.17% | N | 10.21% |

$^1$H NMR (DMSO-d$_6$) δ [ppm]:
1.05-2.18 (m, 10H, CH$_2$-cyclohexyl), 1.62 (s, 3H, 5'-CH$_3$), 4.41 (tt, J=12.2, 3.7 Hz, 1H, CH-cyclohexyl), 7.53-7.58 (m, 1H, 6-H), 9.70 (s, 1H, N—H), 11.60 (s, 1H, 3'-H).

$^{13}$C NMR (DMSO-d$_6$) δ [ppm]:
22.70 (5'-CH$_3$), 25.10, 25.88, 25.98, 28.22, 29.20 (CH$_2$-cyclohexyl), 54.31 (CH-cyclohexyl), 60.24 (C-5'), 111.94 (d, $^2$J (C, F)=20.3 Hz, C-6), 118.19-118.37 (m, C-1), 140 (m, $^1$J (C, F)=240 Hz, C-3), 142 (m, $^1$J (C, F)=250 Hz, C-4), 145 (m, $^1$J (C, F)=250 Hz, C-5), 146 (m, $^1$J (C, F)=240 Hz, C-2), 149.79 (C-2'), 161.60 (C=O), 169.34, 170.45 (C-4', C-6').

MS (EI):
m/z (%): 415 (M$^+$, 11).

N-(1-Cyclohexyl-5-ethyl-hexahydro-2,4,6-trioxo-5-pyrimidinyl)-2,3,4,5-tetrafluorobenzamide (20i)

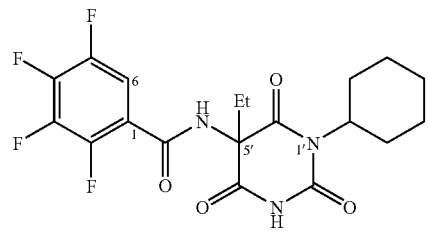

Compound 20i was prepared by the same method described for 20f using 5-amino-1-cyclohexyl-5-ethylbarbituric acid (0.51 g, 2 mmol). The crude 1-cyclohexyl-5-ethyl-5-(tetrafluorobenzamido)barbituric acid (20i) was obtained as yellow crystals and did not require further purification.

| Yield (crude product): | | | Melting point (crude product): | | | |
|---|---|---|---|---|---|---|
| 0.62 g, (72%) | | | 210-212° C. | | | |
| Elemental analysis: | | | | | | |
| $C_{19}H_{19}F_4N_3O_4$ | calcd.: | C | 53.15% | H | 4.46% | N | 9.79% |
| (429.37 g/mol) | found.: | C | 53.30% | H | 4.72% | N | 10.19% |

$^1$H NMR (DMSO-d$_6$) δ [ppm]:
0.89 (t, J=7.6 Hz, 3H, 5'-CH$_2$CH$_3$), 1.02-2.20 (m, 10H, CH$_2$-cyclohexyl), 2.01 (q, J=7.6 Hz, 2H, 5'-CH$_2$CH$_3$), 4.45 (tt, J=12.2, 3.6 Hz, 1H, CH-cyclohexyl), 7.51-7.57 (m, 1H, 6-H), 9.60 (s, 1H, N—H), 11.69 (s, 1H, 3'-H).

$^{13}$C NMR (DMSO-d$_6$) δ [ppm]:
7.75 (5'-CH$_2$CH$_3$), 25.06, 25.88, 25.96, 28.31, 29.21 (CH$_2$-cyclohexyl), 29.96 (5'-CH$_2$CH$_3$), 54.37 (CH-cyclohexyl), 64.10 (C-5'), 111.98 (d, $^2$J (C, F)=20.1 Hz, C-6), 118.35-

118.53 (m, C-1), 140 (m, $^1$J (C, F)=250 Hz, C-3), 141 (m, $^1$J (C, F)=250 Hz, C-4), 145 (m, $^1$J (C, F)=254 Hz, C-5), 146 (m, $^1$J (C, F)=245 Hz, C-2), 149.88 (C-2'), 161.77 (C=O), 168.60, 169.63 (C-4', C-6').

MS (EI):
m/z (%): 429 (M$^+$, 10).

N-(5-Ethyl-hexahydro-2,4,6-trioxo-1-phenyl-5-pyrimidinyl)-2,3,4,5-tetrafluorobenzamide (20k)

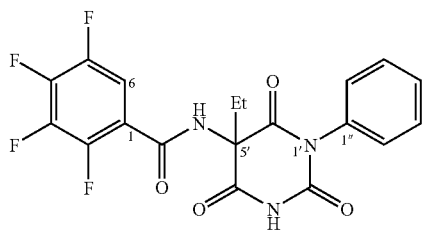

Compound 20k was prepared by the same method described for 20f using 5-amino-5-ethyl-1-phenylbarbituric acid (0.50 g, 2 mmol). The crude 5-ethyl-1-phenyl-5-(tetrafluorobenz-amido)barbituric acid (20k) was obtained as yellow crystals that were pure.

| Yield (crude product): 0.46 g, (54%) | | | Melting point (crude product): 210-215° C. | | | | |
|---|---|---|---|---|---|---|---|
| Elemental analysis: | | | | | | | |
| $C_{19}H_{13}F_4N_3O_4$ (423.32 g/mol) | calcd.: found.: | C C | 53.91% 54.58% | H H | 3.10% 3.36% | N N | 9.93% 9.73% |

$^1$H NMR (DMSO-d$_6$) δ [ppm]:
1.03 (t, J=7.6 Hz, 3H, 5'-CH$_2$CH$_3$), 2.19 (q, J=7.6 Hz, 2H, 5'-CH$_2$CH$_3$), 7.21-7.22 (m, 2H, $\overline{2''}$-H, 6''-H), 7.42-7.51 (m, 3H, $\overline{3''}$-H, 4''-H, 5''-H), 7.56-7.61 (m, 1H, 6-H), 9.76 (s, 1H, N—H), 12.02 (s, 1H, 3'-H).

$^{13}$C NMR (DMSO-d$_6$) δ [ppm]:
7.98 (5'-CH$_2$CH$_3$), 29.72 (5'-CH$_2$CH$_3$), 64.07 (C-5'), 112.03 (d, $^2$J (C, F)=21.1 Hz, C-6), 118.18-118.36 (m, C-1), 128.78 (C-2'', C-6''), 128.86 (C-4''), 129.28 (C-3'', C-5''), 134.72 (C-1''), 140 (m, $^1$J (C, F)=258 Hz, C-3), 142 (m, $^1$J (C, F)=249 Hz, C-4), 145 (m, $^1$J (C, F)=256 Hz, C-5), 146 (m, $^1$J (C, F)=246 Hz, C-2), 149.70 (C-2'), 162.16 (C=O), 168.86, 169.48 (C-4', C-6').

MS (EI):
m/z (%): 423 (M$^+$, 35).

Methods of Treatment

Also disclosed are methods for treating undesirable angiogenesis and angiogenesis dependent or associated diseases, in a subject such as an animal, for example a rat, or a human. The method includes administering one or more of the presently described compounds, or a combination of one or more of the compounds and one or more other pharmaceutical agents, to the subject in a pharmaceutically compatible carrier. The administration is made in an amount effective to inhibit the development or progression of angiogenesis and diseases associated with the same. Although the treatment can be used prophylactically in any patient in a demographic group at significant risk for such diseases, subjects can also be selected using more specific criteria, such as a definitive diagnosis of the condition.

The vehicle in which the drug is delivered can include pharmaceutically acceptable compositions of the drugs, using methods well known to those with skill in the art. Any of the common carriers, such as sterile saline or glucose solution, can be utilized with the drugs disclosed herein. Routes of administration include but are not limited to oral and parenteral routes, such as intravenous (iv), intraperitoneal (ip), rectal, topical, ophthalmic, nasal, and transdermal.

The drug may be administered in a suitable manner now known or later developed, e.g., orally or intravenously, in any conventional medium. For example, intravenous injection may be by an aqueous saline medium. The medium may also contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like. A more complete explanation of parenteral pharmaceutical carriers can be found in *Remington: The Science and Practice of Pharmacy* (19$^{th}$ Edition, 1995) in chapter 95.

Examples, of other pharmaceutical compositions can be prepared with conventional pharmaceutically acceptable carriers, adjuvants and counterions as would be known to those of skill in the art. The compositions are preferably in the form of a unit dose in solid, semi-solid and liquid dosage forms such as tablets, pills, powders, liquid solutions or suspensions.

The compounds illustrated herein are ideally administered as soon as possible after detected unwanted angiogenesis. For example, once unwanted angiogenesis has been confirmed or the presence of a tumor has been identified, a therapeutically effective amount of the drug is administered. The dose can be given orally or by frequent bolus administration.

Therapeutically effective doses of the presently described compounds can be determined by one of skill in the art, with a goal of achieving a desired level of anti-angiogenesis as illustrated in the foregoing examples. In one embodiment, an anti-angiogenic effective amount is an amount sufficient to achieve a statistically significant inhibition of angiogenesis compared to a control. Angiogenesis can be readily assessed using an assay, e.g., the assay described in the Examples below. Alternatively, angiogenesis can be determined in another assay or by direct or indirect signs of angiogenesis in a patient.

The relative toxicities of the compounds make it possible to administer in various dosage ranges. An example of such a dosage range is from about 0.5 to about 50 mg/kg body weight orally in single or divided doses. Another example of a dosage range is from about 1.0 to about 25 mg/kg body weight orally in single or divided doses. For oral administration, the compositions are, for example, provided in the form of a tablet containing from about 25 to about 500 mg of the active ingredient, particularly 100 mg of the active ingredient for the symptomatic adjustment of the dosage to the subject being treated.

The specific dose level and frequency of dosage for any particular subject may be varied and will depend upon a variety of factors, including the activity of the specific compound, the extent of existing angiogenic activity, the age, body weight, general health, sex, diet, mode and time of administration, rate of excretion, drug combination, and severity of the condition of the host undergoing therapy.

The pharmaceutical compositions can be used in the treatment of a variety of diseases mediated by angiogenesis. Examples of such angiogenic-dependent diseases include all types of cancer, ocular neovascular disease, tumor formation and metastasis in tumors such as myeloma, rhabdomyosarcomas, retinoblastoma, Ewing sarcoma, neuroblastoma, osteosarcoma, colon, prostate, head and neck, breast, bladder, liver, pancreatic, lung, CNS, and blood-born tumors such as leukemia, also diseases such as hemangioma, ulcerative colitis, Crohn's disease, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eale's disease, Bechet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy.

Combination Therapy

Also disclosed herein are combinations of the presently described compounds and/or combination of the same with various other angiogenesis inhibitor compounds. For example, the presently described compounds may be administered in combination with effective doses of other anti-angiogenic agents. The term "administration" refers to both concurrent and sequential administration of the active agents. Examples of anti-angiogenic agents that can be used in combination with the thalidomide analogs of the present invention are TNP-470, carbonic anhydrase inhibitors, endostatin, angiostatin, 2-methoxyestradiol, IMiD (Immune-modulating inhibitor drug) CC5013, matrix metalloproteinase inhibitors, and COL-3. In addition, the presently described compound may be used in combination with other forms of cancer therapy (e.g., chemotherapy, radiation therapy, hormonal therapy).

Example 1

Anti-Angiogenic Activity Analysis Results for Selected Presently Disclosed Compounds Measured Utilizing Rat Aortic Rings The anti-angiogenic activity of the compounds was tested following the procedure described in Lepper, E. R., Ng, S. S., Gutschow, M., Weiss, M., Hauschildt, S., Hecker, T. K., Luzzio, F. A., Eger, K., Figg, W. D., *J. Med. Chem.* 2004, Comparative molecular field analysis and comparative molecular similarity indices analysis of thalidomide analogues as angiogenesis inhibitors; 47(9):2219-27. Twelve-well tissue culture-grade plates were covered with 250 µL Matrigel and allowed to gel for 30 to 45 minutes at 37° C., 5% $CO_2$. Thoracic aortas were excised from 6- to 8-week-old male Sprague-Dawley rats, and the fibroadipose tissue was removed. The aortas were cut into 1 mm-long cross-sections and placed on the Matrigel coated wells. They were then covered with an additional 250 µL Matrigel and allowed to gel for 30 to 45 minutes at 37° C., 5% $CO_2$. The rings were cultured for 24 hours in 1 mL EBM-2. After 24 hours, the medium was removed and replaced with 1 mL EBM-2 (Clonetics Corp.), supplemented with fetal bovine serum (2%), ascorbic acid, hydrocortisone, heparin, and amphotericin. Each selected compound was dissolved in DMSO and added to the EBM-2, before it was added to the well. Each selected compound was administered daily for four days at a daily dosage of 50 µM. Photos were taken on Day 5. DMSO alone was used as a control baseline. Carboxyamidotriazole ("CAI" from NCI, Bethesda, Md.) was used as a positive control. The vascular outgrowth was quantified using Adobe Photoshop (Adobe Systems, Inc., San Jose, Calif.) and the results are provided below in Tables 1 and 2.

TABLE 1

Inhibition data from rat aortic ring microvessel assay for phthalimides 19, at a concentration of 50 µM.

| No. | Structure | Average of Growth [%] | Standard Deviation of Growth [%] |
|-----|-----------|-----------------------|----------------------------------|
|     | DMSO      | 100                   | 0                                |
|     | CAI       | 4.03                  | 7.77                             |
| 19a | 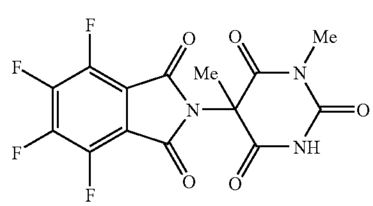          | 0.12                  | 0.01                             |
| 19b | 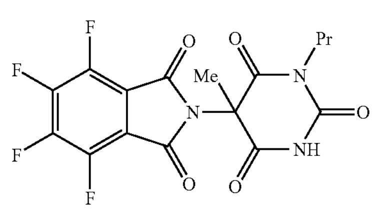          | 0.13                  | 0.05                             |

TABLE 1-continued

Inhibition data from rat aortic ring microvessel assay for phthalimides 19, at a concentration of 50 μM.

| No. | Structure | Average of Growth [%] | Standard Deviation of Growth [%] |
| --- | --- | --- | --- |
| 19c | 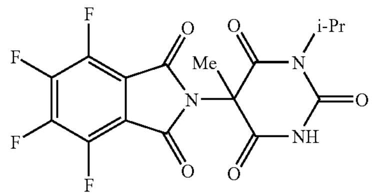 | 0.14 | 0.05 |
| 19d | 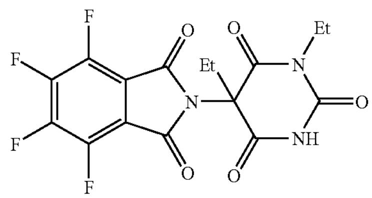 | 0.13 | 0.05 |
| 19e | 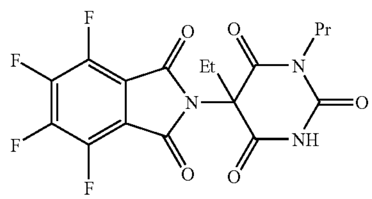 | 0.12 | 0.01 |
| 19f | 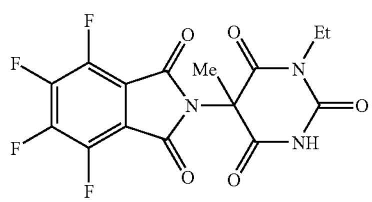 | 23.79 | 3.26 |
| 19g | 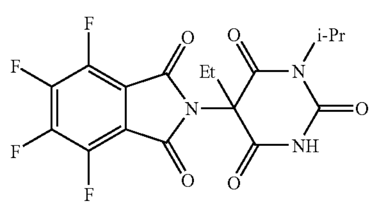 | 0.13 | 0.05 |
| 19h | 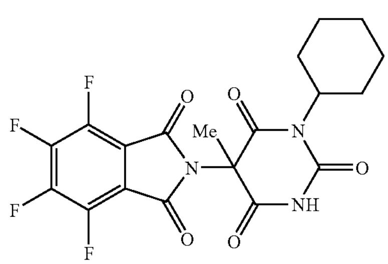 | 11.76 | 1.80 |

TABLE 1-continued

Inhibition data from rat aortic ring microvessel assay for phthalimides 19, at a concentration of 50 μM.

| No. | Structure | Average of Growth [%] | Standard Deviation of Growth [%] |
|---|---|---|---|
| 19i | 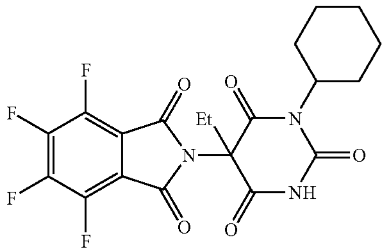 | 11.19 | 2.93 |
| 19k | | 24.25[a] | 22.54[a] | a-Compound 19k is a prior art compound included in Table 1 for comparative purposes. The rat aortic ring inhibition data for compound 19k is reported in Lepper, E.R., Ng, S.S., Gutschow, M., Weiss, M., Hauschildt, S., Hecker, T.K., Luzzio, F.A., Eger, K., Figg, W.D., J. Med. Chem. 2004, Comparative molecular field analysis and comparative molecular similarity indices analysis of thalidomide analogues as angiogenesis inhibitors; 47(9):2219-27 (compound 19k is compound 14 in the Lepper et al. article).

TABLE 2

Inhibition data from rat aortic ring microvessel assay for tetrafluorobenzamides 20, at a concentration of 50 μM.

| No. | Structure | Average of Growth [%] | Standard Deviation of Growth [%] |
|---|---|---|---|
| | DMSO | 100 | 0 |
| | CAI | 4.03 | 7.77 |
| 20a | 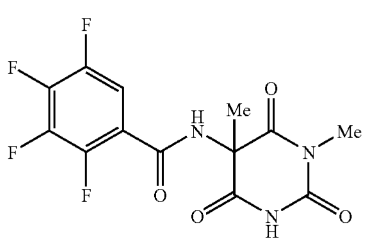 | 58.28 | 23.96 |
| 20b | 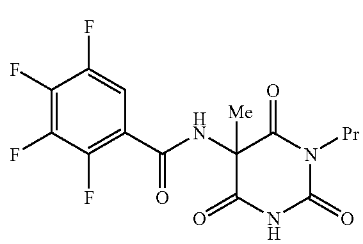 | 23.06 | — |

TABLE 2-continued

Inhibition data from rat aortic ring microvessel assay for tetrafluorobenzamides 20, at a concentration of 50 μM.

| No. | Structure | Average of Growth [%] | Standard Deviation of Growth [%] |
|---|---|---|---|
| 20c | (tetrafluorobenzamide with Me, i-Pr substituents) | 5.63 | 7.93 |
| 20d | (tetrafluorobenzamide with Et, Et substituents) | 31.06 | 2.79 |
| 20e | (tetrafluorobenzamide with Et, Pr substituents) | 0.19 | 0.16 |
| 20f | (tetrafluorobenzamide with Me, Et substituents) | 16.76 | 12.87 |
| 20g | (tetrafluorobenzamide with Et, i-Pr substituents) | 0.10 | 0.04 |

TABLE 2-continued

Inhibition data from rat aortic ring microvessel assay for tetrafluorobenzamides 20, at a concentration of 50 μM.

| No. | Structure | Average of Growth [%] | Standard Deviation of Growth [%] |
|---|---|---|---|
| 20h | (structure) | 16.49 | 9.11 |
| 20i | (structure) | 9.73 | 2.84 |
| 20k | (structure) | 18.06 | 15.95 |

The data in Tables 1 and 2 demonstrate that the compounds disclosed herein possess unexpectedly superior anti-angiogenic properties. The inhibition of angiogenesis by previously reported tetrafluorinated compounds has been shown to be predictive of the thalidomide analogs' efficacy in anti-cancer activity (see, e.g., Ng et al., Antitumor Effects of Thalidomide Analogs in Human Prostate Cancer Xenografts Implanted in Immunodeficient Mice, *Clinical Cancer Research* Vol. 10, 4192-4197 (2004); Kumar et al, Antimyeloma activity of two novel N-substituted and tetrafluorinated thalidomide analogs, *Leukemia* (2005) 19, 1253-1261).

Example 2

Cell Proliferation Assays

Figure 5:
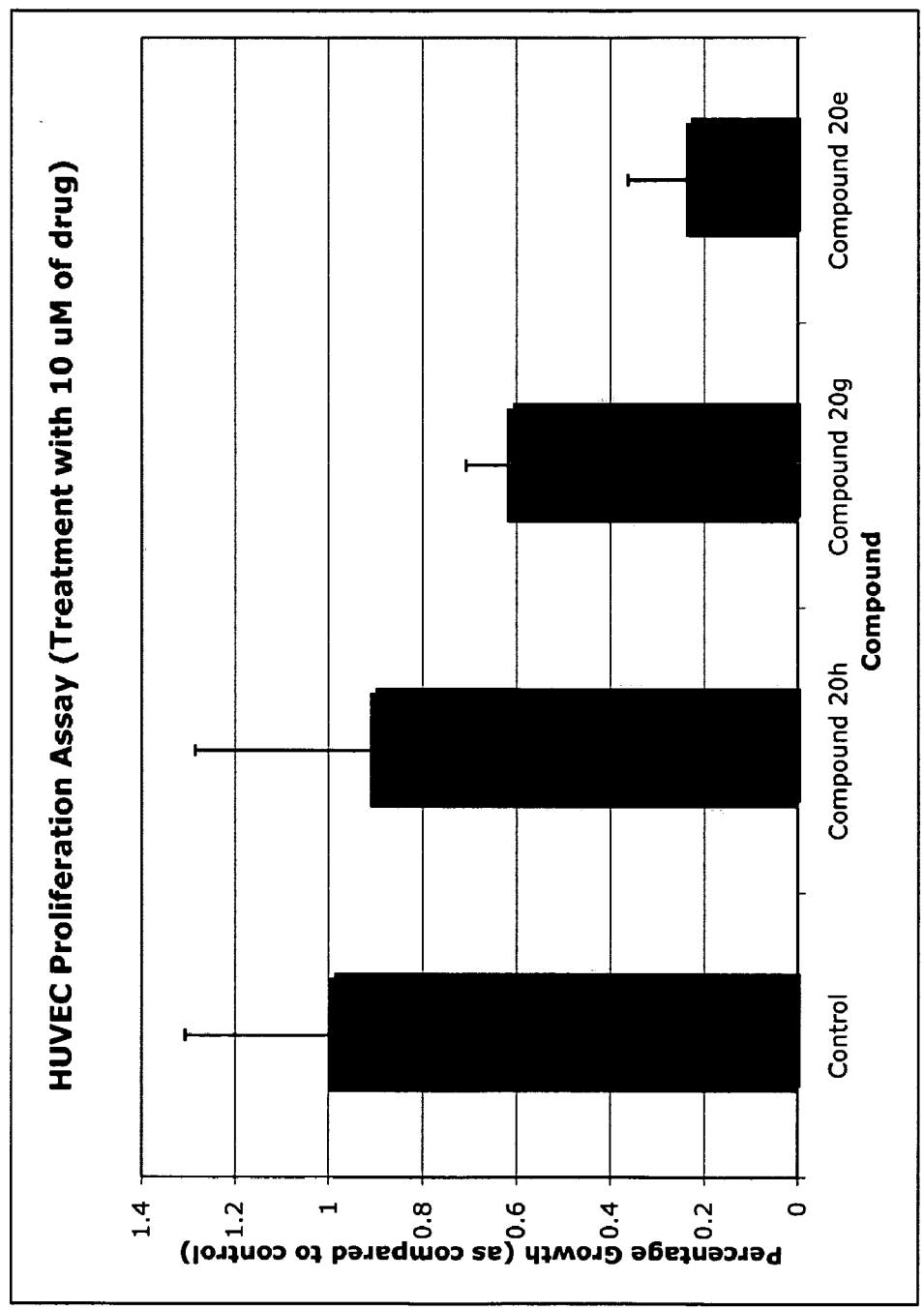
FIG. 5 is a graph depicting the results of HUVEC cell proliferation assays.
Figure 6:
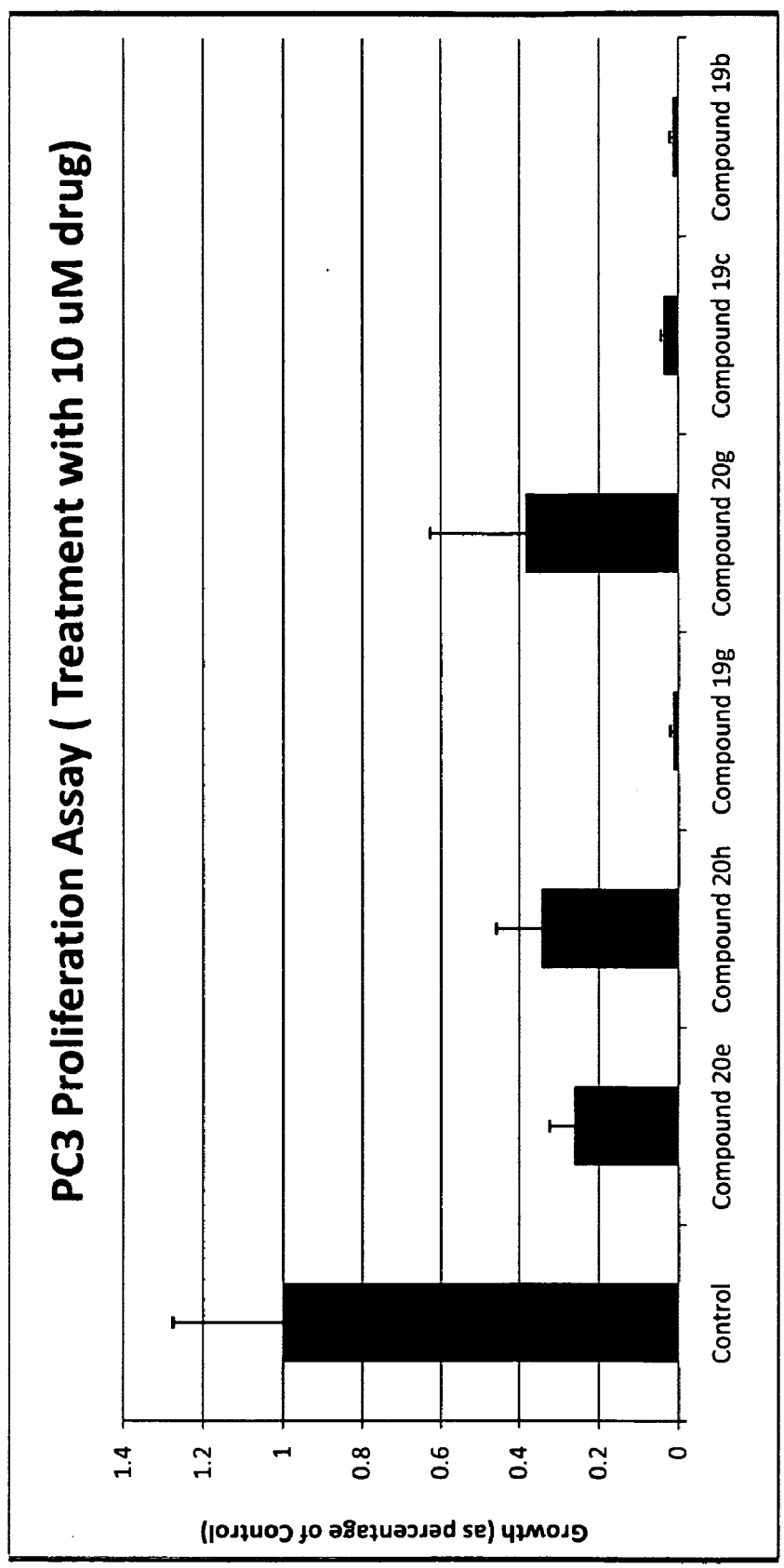
FIG. 6 is a graph depicting the results of PC3 cell proliferation assays.

Human umbilical vein endothelial cells (HUVECs (Clonetics)) were maintained in EGM-II, supplemented with a Bullet-Kit (Clonetics). Human prostate cancer cell lines (PC3s (ATCC)) were maintained in RPMI-1640, supplemented with 10% fetal bovine serum. Both cell lines were incubated at 37° C., in a 5% $CO_2$ atmosphere. Cells were seeded onto 12-well plates at a density of 30,000 cells/well and allowed to attach overnight at 37° C. and 5% $CO_2$. The culture medium was then aspirated, and fresh culture medium containing either the vehicle (0.5% DMSO) or drug solution in 0.5% DMSO was added. After 24 hours, media was removed, then cells were trypsinized and counted with a hemocytometer, using trypan blue to exclude non-viable cells. Each compound was tested in triplicate and the cell count was normalized to the controls, to give the % growth. The results are shown below in Tables 3 and 4, and in FIGS. 5 and 6.

TABLE 3

HUVEC Proliferation Assay

| Compound | Average of Growth [%] | Standard Deviation of Growth [%] |
|---|---|---|
| DMSO control | 100.00 | 30.69 |
| 20h | 91.14 | 37.40 |
| 20g | 62.03 | 8.77 |
| 20e | 24.05 | 12.21 |

TABLE 4

PC3 Proliferation Assay

| Compound | Average of Growth [%] | Standard Deviation of Growth [%] |
|---|---|---|
| DMSO control | 100.00 | 27.49 |
| 19g | 1.50 | 0.65 |
| 19c | 3.75 | 0.65 |
| 19b | 1.50 | 0.65 |
| 20e | 26.27 | 6.20 |
| 20h | 34.52 | 11.33 |
| 20g | 38.46 | 24.38 |

TABLE 5

| | HUVEC and PC3 Proliferation Assays | | | | | | | |
|---|---|---|---|---|---|---|---|---|
| | 24 h incubation; CCK-8 counting | | | | | | | |
| | HUVEC Growth (5 uM) (Control = 100%) | | HUVEC Growth (10 uM) (Control = 100%) | | PC3 Growth (5 uM) (Control = 100%) | | PC3 Growth (10 uM) (Control = 100%) | |
| Compound | Mean | SD | Mean | SD | Mean | SD | Mean | SD |
| 20d | 11.46% | 0.41% | 14.53% | 1.39% | n/a | n/a | 87.73% | 16.68% |
| 19f | 27.17% | 7.28% | 9.00% | 3.42% | 25.95% | 8.90% | 10.94% | 3.74% |
| 19e | 1.68% | 0.43% | 2.14% | 1.01% | 31.02% | 6.23% | 9.67% | 2.30% |

The experiments for the data in Table 5 was performed as described above, except that the Table 5 experiments were performed in 96-2311 plates (at two concentrations), and the CCK-8 Cell Counting Kit (Dajindo Technologies) was utilized after treating for 24 hours.

In view of the many possible embodiments to which the principles of the disclosure may be applied, it should be recognized that the illustrated embodiments are only preferred examples and should not be taken as limiting the scope of the invention. Rather, the scope of the invention is defined by the following claims. We therefore claim as our invention all that comes within the scope and spirit of these claims.

What is claimed is:

1. A compound, or a pharmaceutically acceptable salt thereof, having the following structure:

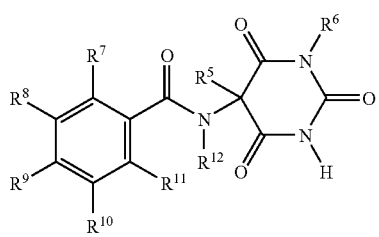

Formula I wherein
(i) $R^5$ and $R^6$ are each independently H, alkyl, cycloalkyl, aryl, hydroxyl or alkenyl; $R^7$-$R^{11}$ are each F or Cl; and $R^{12}$ is H or alkyl; or
(ii) $R^5$ and $R^6$ are each independently H, alkyl, cycloalkyl, aryl, hydroxyl or alkenyl; $R^7$-$R^{10}$ are each F or Cl; $R^{11}$ is H; and $R^{12}$ is H or alkyl; or
(iii) $R^5$ and $R^6$ are each independently alkyl or cycloalkyl; $R^7$-$R^{10}$ are each F or Cl; and $R^{11}$ and $R^{12}$ together form a 5-member or 6-member ring structure.

2. The compound, or a pharmaceutically acceptable salt thereof, of claim 1, wherein the compound has a structure represented by:

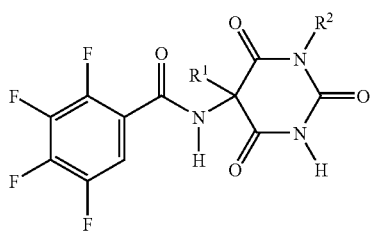

Formula II wherein $R^1$ is H, alkyl, or cycloalkyl; and $R^2$ is H, alkyl, cycloalkyl, aryl, hydroxyl, or alkenyl.

3. The compound of claim 2, wherein $R^1$ is an alkyl selected from methyl, ethyl and propyl and $R^2$ is an alkyl selected from methyl, ethyl and propyl; a cyclohexyl; or a phenyl.

4. The compound of claim 2, wherein the compound has the structure:

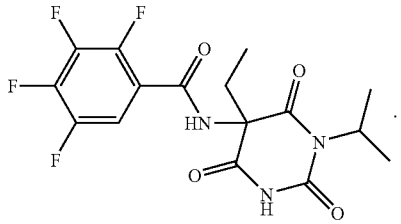

5. The compound of claim 2, wherein the compound has the structure:

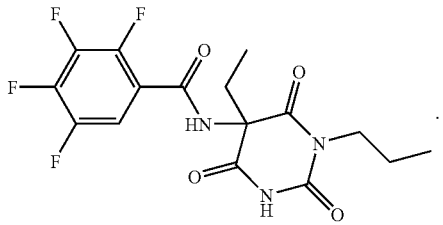

6. The compound of claim 2, wherein the compound has the structure:

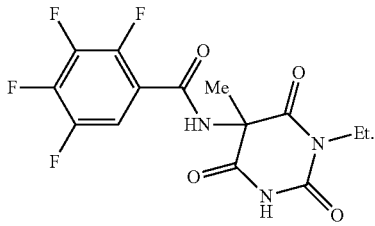

7. The compound of claim 2, wherein the compound has the structure:

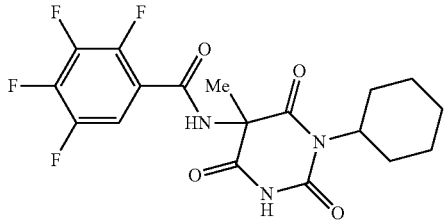

8. The compound of claim 2, wherein the compound has the structure:

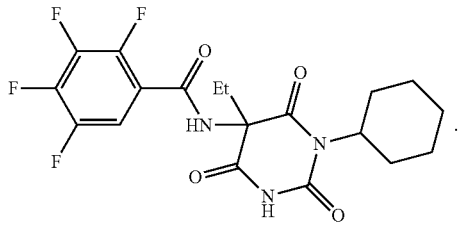

9. The compound of claim 2, wherein the compound has the structure:

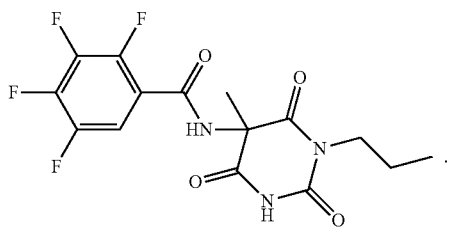

10. The compound of claim 2, wherein the compound has the structure:

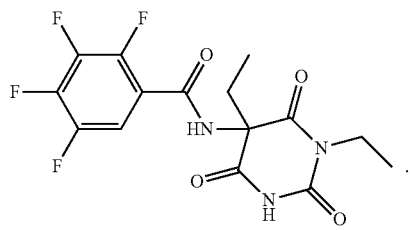

11. The compound of claim 2, wherein the compound has the structure:

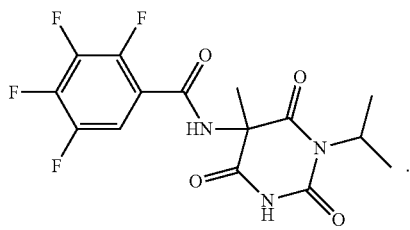

12. The compound of claim 2, wherein the compound has the structure:

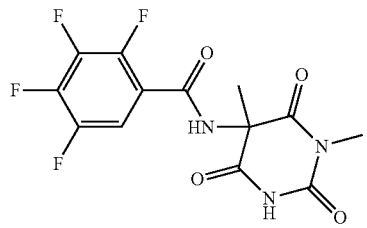

13. The compound of claim 2, wherein the compound has the structure:

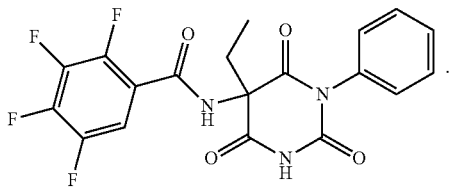

14. A compound, or a pharmaceutically acceptable salt thereof, wherein the compound has a structure represented by:

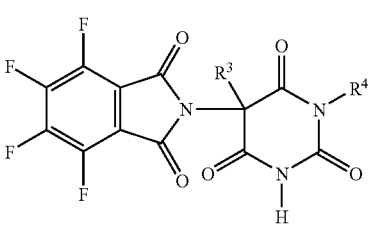

Formula III wherein $R^3$ is H, alkyl or cycloalkyl; and $R^4$ is H, alkyl, cycloalkyl, hydroxyl or alkenyl.

15. The compound of claim 14, wherein $R^3$ is an alkyl selected from methyl, ethyl and propyl and $R^4$ is an alkyl selected from methyl, ethyl and propyl; or a cyclohexyl.

16. The compound of claim 14, wherein the compound has the structure:

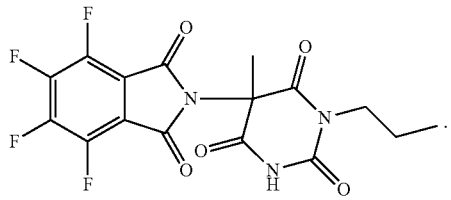

17. The compound of claim 14, wherein the compound has the structure:

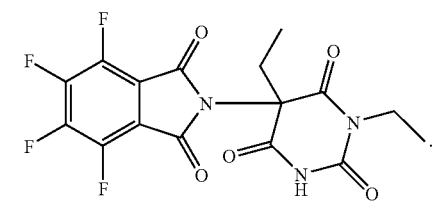

18. The compound of claim 14, wherein the compound has the structure:

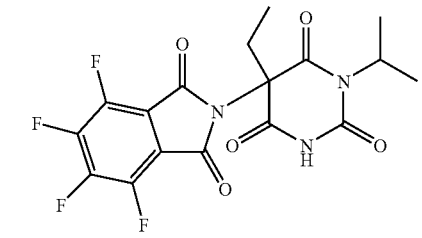

19. The compound of claim 14, wherein the compound has the structure:

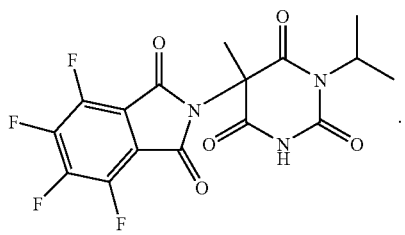

20. The compound of claim 14, wherein the compound has the structure:

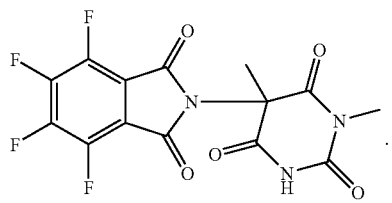

21. The compound of claim 14, wherein the compound has the structure:

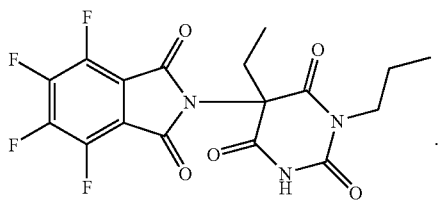

22. The compound of claim 14, wherein the compound has the structure:

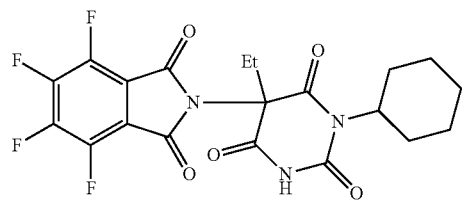

23. The compound of claim 14, wherein the compound has the structure:

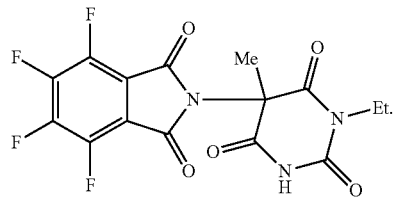

24. The compound of claim 14, wherein the compound has the structure:

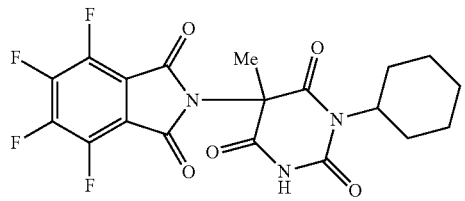

25. A pharmaceutical composition comprising the compound of claim 1, or a pharmaceutically acceptable salt thereof, and a pharmaceutically acceptable carrier.

26. The pharmaceutical composition of claim 25, comprising the compound of claim 14.

27. The pharmaceutical composition of claim 25, comprising the compound of claim 21.

28. The compound of claim 1, wherein the compound has a structure selected from:

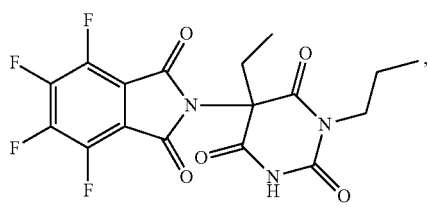

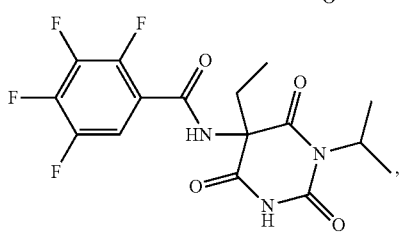

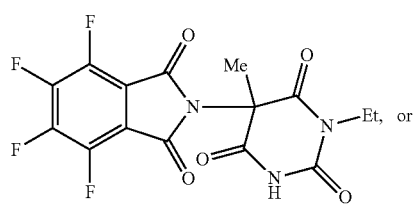

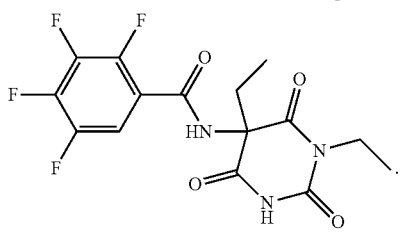

29. The compound of claim 1, wherein the compound has a structure selected from:

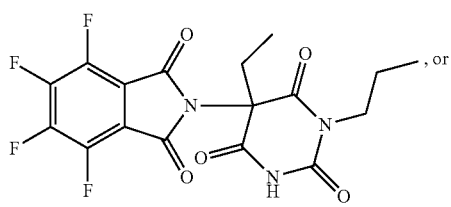

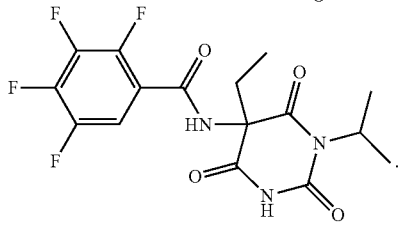

30. The pharmaceutical composition of claim 25, wherein the compound has a structure selected from:
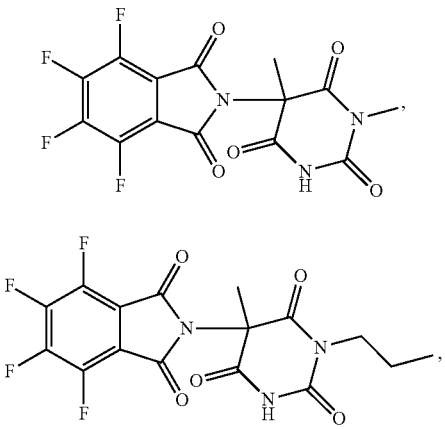
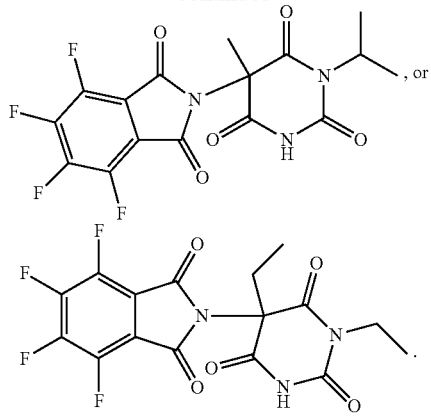
31. A pharmaceutical composition comprising the compound of claim 2, or a pharmaceutically acceptable salt thereof, and a pharmaceutically acceptable carrier.
* * * * *